(12) United States Patent
Chen et al.

(10) Patent No.: US 7,189,582 B2
(45) Date of Patent: Mar. 13, 2007

(54) COMPOSITIONS AND METHODS FOR DETECTION OF SIROLIMUS

(75) Inventors: Jian Chen, Sunnyvale, CA (US); Holger Keim, Wyckoff, NJ (US); Hshiou-ting Liu, Milpitas, CA (US); Yi Feng Zheng, Wilmington, DE (US); Yali Yang, Bear, DE (US); Cathy K. Worley, Washington, DC (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 11/116,928

(22) Filed: Apr. 27, 2005
(Under 37 CFR 1.47)

(65) Prior Publication Data

US 2006/0246518 A1    Nov. 2, 2006

(51) Int. Cl.
G01N 33/532 (2006.01)
C07K 16/44 (2006.01)
C07K 1/13 (2006.01)
C07D 267/00 (2006.01)

(52) U.S. Cl. .................. 436/544; 436/56; 436/815; 435/7.1; 435/7.93; 530/389.8; 530/403; 530/405; 530/807; 540/456

(58) Field of Classification Search .............. 435/7.1, 435/961, 548, 975, 7.93; 424/193.1; 540/456; 436/544, 546, 56, 815; 530/403, 405, 388.9, 530/389.8, 807
See application file for complete search history.

(56) References Cited

U.S. PATENT DOCUMENTS

| | | |
|---|---|---|
| 4,153,447 A | 5/1979 | Boroschewski et al. |
| 4,683,136 A | 7/1987 | Milich et al. |
| 4,883,751 A | 11/1989 | Gitel et al. |
| 4,920,218 A | 4/1990 | Askin et al. |
| 5,023,264 A | 6/1991 | Caufield et al. |
| 5,068,323 A | 11/1991 | Wyvratt, Jr. et al. |
| 5,118,677 A | 6/1992 | Caufield |
| 5,118,678 A | 6/1992 | Kao et al. |
| 5,120,725 A | 6/1992 | Kao et al. |
| 5,120,726 A | 6/1992 | Failli et al. |

(Continued)

FOREIGN PATENT DOCUMENTS

EP    0 364 032    10/1989

(Continued)

OTHER PUBLICATIONS

Yohannes, et al., "Degradation of Rapamycin: Synthesis of . . . ", Tetrahedron Letters, (1993) vol. 34, No. 13, pp. 2075-2078.

(Continued)

*Primary Examiner*—Long V. Le
*Assistant Examiner*—Shafiqul Haq
(74) *Attorney, Agent, or Firm*—Theodore J. Leitereg

(57) ABSTRACT

Compounds are disclosed comprising a moiety, such as a poly(amino acid), a non-poly(amino acid) label moiety, or a non-poly(amino acid) immunogenic carrier, linked to a sirolimus compound at position 26 or at position 32. Such sirolimus compounds comprising an immunogenic carrier can be employed to raise both polyclonal and monoclonal antibodies to the sirolimus compound. Polyclonal antibodies are also disclosed, which are raised against a compound wherein a moiety, such as a poly(amino acid), a non-poly(amino acid) label moiety, or a non-poly(amino acid) immunogenic carrier, is linked to a sirolimus compound at position 32. The above antibodies and sirolimus compounds comprising a label can be used in assays for the detection of sirolimus compounds.

17 Claims, 9 Drawing Sheets

U.S. PATENT DOCUMENTS

| | | | |
|---|---|---|---|
| 5,151,413 A | 9/1992 | Caufield et al. |
| 5,169,773 A | 12/1992 | Rosenthaler et al. |
| 5,194,447 A | 3/1993 | Kao |
| 5,233,025 A | 8/1993 | Miyazaki et al. |
| 5,258,389 A | 11/1993 | Goulet et al. |
| 5,260,300 A | 11/1993 | Hu |
| 5,283,190 A | 2/1994 | Traish et al. |
| 5,302,584 A | 4/1994 | Kao et al. |
| 5,354,845 A | 10/1994 | Soldin |
| 5,362,718 A | 11/1994 | Skotnicki et al. |
| 5,362,735 A | 11/1994 | Luengo |
| 5,373,014 A | 12/1994 | Failli et al. |
| 5,378,836 A | 1/1995 | Kao et al. |
| 5,385,909 A | 1/1995 | Nelson et al. |
| 5,391,730 A | 2/1995 | Skotnicki et al. |
| 5,411,967 A | 5/1995 | Kao et al. |
| 5,416,086 A | 5/1995 | Kao et al. |
| 5,432,183 A | 7/1995 | Schulte |
| 5,455,249 A | 10/1995 | Skotnicki et al. |
| 5,484,790 A | 1/1996 | Failli et al. |
| 5,484,791 A | 1/1996 | Failli et al. |
| 5,486,522 A | 1/1996 | Failli et al. |
| 5,486,523 A | 1/1996 | Failli et al. |
| 5,486,524 A | 1/1996 | Failli et al. |
| 5,488,054 A | 1/1996 | Failli et al. |
| 5,489,595 A | 2/1996 | Failli et al. |
| 5,498,597 A | 3/1996 | Burakoff et al. |
| 5,503,987 A | 4/1996 | Wagner et al. |
| 5,504,091 A | 4/1996 | Molnar-Kimber et al. |
| 5,508,399 A | 4/1996 | Kao et al. |
| 5,525,523 A | 6/1996 | Soldin |
| 5,525,610 A | 6/1996 | Caufield et al. |
| 5,530,007 A | 6/1996 | Kao et al. |
| 5,559,120 A | 9/1996 | Kao et al. |
| 5,563,145 A | 10/1996 | Failli et al. |
| 5,583,139 A | 12/1996 | Or et al. |
| 5,648,361 A | 7/1997 | Holt et al. |
| 5,656,434 A | 8/1997 | Terano et al. |
| 5,661,156 A | 8/1997 | Holt et al. |
| 5,665,772 A | 9/1997 | Cottens et al. |
| 5,672,605 A | 9/1997 | Or et al. |
| 5,677,295 A | 10/1997 | Failli et al. |
| 5,728,710 A | 3/1998 | Luengo |
| 5,780,307 A | 7/1998 | Soldin |
| 5,912,253 A | 6/1999 | Cottens et al. |
| 5,922,730 A | 7/1999 | Hu et al. |
| 5,952,320 A | 9/1999 | Davidsen et al. |
| 5,985,890 A | 11/1999 | Cottens et al. |
| 6,054,303 A | 4/2000 | Davalian et al. |
| 6,200,985 B1 | 3/2001 | Cottens et al. |
| RE37,421 E | 10/2001 | Holt et al. |
| 6,328,970 B1 * | 12/2001 | Molnar-Kimber et al. ............. 424/184.1 |
| 6,455,518 B2 | 9/2002 | Zenke et al. |
| 6,541,612 B2 | 4/2003 | Molnar-Kimber et al. |
| 6,635,745 B2 | 10/2003 | Sedrani et al. |
| 6,677,357 B2 | 1/2004 | Zhu et al. |
| 6,709,873 B1 | 3/2004 | Yatscoff et al. |
| 2001/0010920 A1 | 8/2001 | Molnar-Kimber et al. |
| 2005/0208607 A1 * | 9/2005 | Roberts et al. ............. 435/7.92 |

FOREIGN PATENT DOCUMENTS

| | | |
|---|---|---|
| EP | 0 401 747 B1 | 6/1990 |
| EP | 0 467 606 A1 | 7/1991 |
| EP | 0 509 795 A2 | 4/1992 |
| EP | 0 867 438 B1 | 9/1993 |
| EP | 0 593 227 A1 | 10/1993 |
| JP | 05-112573 A | 5/1993 |
| JP | 06-211870 A | 8/1994 |
| JP | 11-240884 A | 9/1999 |
| WO | WO 91/10907 | 7/1991 |
| WO | WO 92/19745 | 11/1992 |
| WO | WO 94/09010 | 4/1994 |
| WO | WO 94/24304 | 10/1994 |
| WO | WO 94/25022 | 11/1994 |
| WO | WO 94/25072 | 11/1994 |
| WO | WO 94/25468 | 11/1994 |

OTHER PUBLICATIONS

Steffan, et al., "Base Catalyzed Degradations of Rapamycin", Tetrahedron Letters (1993), vol. 34, No. 23, pp. 3699-3702.

Luengo, et al., "Studies on the Chemistry of Rapamycin: Novel Transformations . . . ", Tetrahedron Letters (1993), vol. 34, No. 6, pp. 991-994.

D. Yohannes and S. Danishefsky, "Degradation of Rapamycin: Retrieval . . . ", Tetrahedron Letters, (1992), vol. 33, No. 49, pp. 7469-7472.

Trepanier, et al., "Rapamycin: Distribution, Pharmacokinetics . . . ", Clinical Biochemistry, (1998) vol. 31, No. 5, pp. 345-351.

Jones, et al., "An Immunoassay for the Measurement of Sirolimus", Clinical Therapeutics (2000), vol. 22, supp. B, pp. B49-B61.

Davis et al."An Immunophilin-Binding Assay for Sirolimus", Clinical Therapeurtics (2000), vol. 22, supp. B, pp. B62-B70.

Salm, et al., "The Quantification of Sirolimus by High-Performance . . . ", Clinical Therapeutics (2000), vol. 22, supp. B, pp. B71-B85.

* cited by examiner

G6PDH Conjugate Preparation

COMPOSITIONS AND METHODS FOR DETECTION OF SIROLIMUS

BACKGROUND

The invention relates to compounds, methods and kits for the determination of sirolimus compounds such as, for example, rapamycin or derivatives thereof, in samples, such as patient samples, known or suspected to contain such sirolimus compounds.

The body relies upon a complex immune response system to distinguish self from non-self. At times, the body's immune system must be controlled in order to either augment a deficient response or suppress an excessive response. For example, when organs such as kidney, heart, heart-lung, bone marrow, and liver are transplanted in humans, the body will often reject the transplanted tissue by a process referred to as allograft rejection.

In treating allograft rejection, the immune system is frequently suppressed in a controlled manner with drug therapy. Immunosuppressant drugs are carefully administered to transplant recipients in order to help prevent allograft rejection of non-self tissue. Two most commonly administered immunosuppressive drugs to prevent organ rejection in transplant patients are Cyclosporine (CSA) and FK-506 (FK). Another drug that finds use as an immunosuppressant in the United States and other countries is sirolimus, also known as rapamycin. Derivatives of sirolimus are also said to be useful as immunosuppressants. Such derivatives include, for example, Everolimus, and the like.

Rapamycin is a macrocyclic trione antibiotic produced by *Streptomyces hygroscopicus*. Rapamycin is structurally related to the immunosuppressant FK-506 (Tacrolimus) but mechanistically different. Rapamycin has anti-candidal, anti-proliferative and anti-tumor activity. Rapamycin also dampens autoimmune reactions (SLE, adjuvant arthritis, allergic encephalomyelitis). Rapamycin is a potent immunosuppressant that inhibits T and B cell activation by blocking cytokine-mediated events, and inhibits growth factor mediated cell proliferation.

The side effects associated with rapamycin can be controlled in part by carefully controlling the level of the drug present in a patient. Because the distribution and metabolism of rapamycin can vary greatly between patients and because of the wide range and severity of adverse reactions, accurate monitoring of the drug level is essential.

Several derivatives of rapamycin have been prepared in the hope of finding an agent that possesses all of the desired immunosuppressive properties of rapamycin, but whose use results in less side effects. Such derivatives include the preparation of oxime derivatives of rapamycin (U.S. Pat. Nos. 5,672,605; 5,373,014; 5,023,264 and 5,378,836).

Rapamycin and its derivatives are being assessed in a number of clinical trials around the world as immunosuppressive agents. In the trials, therapeutic drug monitoring (TDM) of plasma levels of rapamycin is recommended for all patients, and especially pediatric patients and those with hepatic impairment. TDM is also recommended when potent inducers or inhibitors of the enzyme CYP3A4 are co-administered. In addition, if rapamycin or its derivative is concomitantly administered with cyclosporin, TDM is recommended because pharmacokinetics are altered during drug co-administration. For example, if rapamycin is administered concomitantly with cyclosporin rather than administered four hours apart, rapamycin trough levels increase. For this reason, as well as to limit certain side effects, TDM should allow for better clinical results in selected cases.

Therapeutic monitoring of concentrations of rapamycin and related drugs in blood is required to optimize dosing regimes to ensure maximal immunosuppression with minimal toxicity. Although rapamycin is a highly effective immunosuppressive agent, its use must be carefully managed because the effective dose range is narrow and excessive dosage can result in serious side effects. On the other hand, too little dosage of rapamycin can lead to tissue rejection.

There is, therefore, a continuing need to develop fast and accurate diagnostic methods to measure levels of sirolimus compounds such as rapamycin or a derivative thereof in patients.

SUMMARY

One embodiment of the present invention is a compound comprising a moiety, such as a poly(amino acid) (including poly(amino acid) label moieties and poly(amino acid) immunogenic carriers as well as other proteins), or non-poly (amino acid) label moiety, or a non-poly(amino acid) immunogenic carrier, linked to a sirolimus compound at position 26.

Another embodiment of the present invention is a compound of structure I:

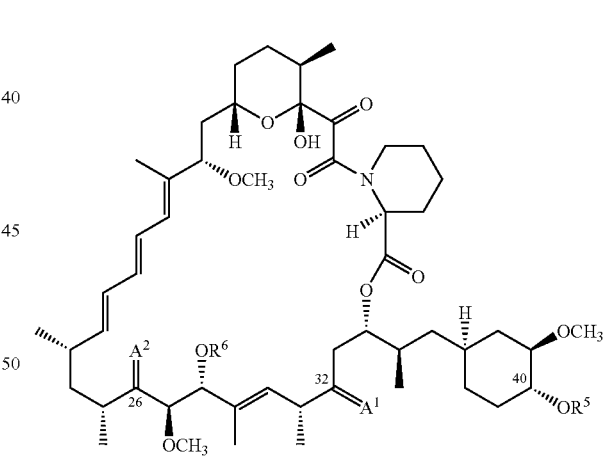

wherein $A^1$ and $A^2$ are independently oxo or a group of the formula:

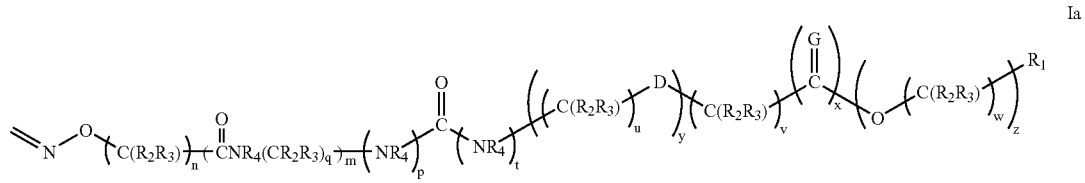

with the proviso that both A¹ and A² cannot be oxo and wherein:

n, q, u, v and w are independently 0 to about 12,
m is 0 or 1,
p is 0 or 1,
t is 0 or 1,
y is 0 to about 5,
x is 0 or 1,
z is 0 or 1,
D is O or S,
G is O or NR², wherein in some embodiments, when A¹ is not oxo, then at least one of m is 1, or t is 1, or y is 1 to about 5, or v is 1 to about 12, or x is 1, or z is 1, or, when A¹ is not oxo, then R¹ is II, R¹ is a functional group or a moiety, such as a poly(amino acid) (including poly(amino acid) label moieties and poly (amino acid) immunogenic carriers as well as other proteins, e.g., antibodies), or non-poly(amino acid) label moiety, or a non-poly(amino acid) immunogenic carrier, or

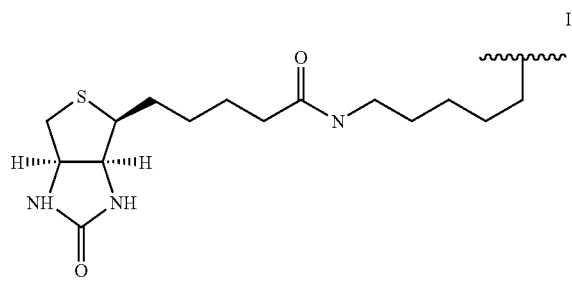

II

R² and R³ are independently selected from hydrogen, $C_{1-10}$ alkyl, benzyl, OH, halogen, $C_{1-6}$ alkoxy; $C_{3-10}$ alkenyl, and $C_{3-10}$ alkynyl, R⁴ is independently hydrogen, $C_{1-10}$ alkyl, benzyl, $C_{3-10}$ alkenyl, $C_{3-10}$ alkynyl; and R⁵ and R⁶ are independently selected from hydrogen; phenyl; substituted phenyl in which the substituents are X, Y and Z; 1- or 2-naphthyl; substituted 1- or 2-naphthyl in which the substituents are X, Y and Z; $C(O)C_{1-6}$ alkyl; $C_{1-10}$ alkyl; $C_3$–$C_{10}$ cycloalkyl; substituted $C_{1-10}$ alkyl in which one or more substituent(s) is(are) selected from hydroxy, oxo, $C_{1-6}$-alkoxy; phenyl, substituted phenyl in which the substituents on phenyl are X, Y and Z and $OC(O)C_{1-6}$ alkyl; $C_{3-10}$ alkenyl; $C_{4-10}$ cycloalkenyl; substituted $C_{3-10}$ alkenyl in which one or more substituent(s) is(are) selected from hydroxy, oxo, $C_{1-6}$-alkoxy, phenyl, substituted phenyl in which the substituents on phenyl are X, Y and Z and $OC(O)C_{1-6}$ alkyl; $C_{3-10}$ alkynyl; and substituted $C_{3-10}$ alkynyl in which one or more substituent(s) is(are) selected from hydroxy, oxo, $C_{1-6}$-alkoxy, phenyl, substituted phenyl, in which the substituents on phenyl are X, Y and Z and $OC(O)C_{1-6}$ alkyl;

X, Y and Z are independently selected from: hydrogen; $C_{1-7}$ alkyl; $C_{2-6}$ alkenyl; halogen; CN; C(O)H; perhalosubstituted groups such as $CF_3$; $SR^7$, wherein $R^7$ is hydrogen, $C_{1-6}$ alkyl, $CF_3$ or phenyl; $SOR^7$, wherein $R^7$ is as defined above; $SO_2R^7$, wherein $R^7$ is as defined above; $CONR^5R^6$, wherein $R^5$ and $R^6$ are as defined above; —$(CH_2)_mOR^8$, wherein $R^8$ is hydrogen, $C_{1-3}$ alkyl; hydroxy-$C_{2-3}$ alkyl, and m is 0–2, and m is 0–2; $C_{1-3}$ hydroxy-$C_{2-3}$ alkyl; $CH(OR^9)(OR^{10})$, wherein $R^9$ and $R^{10}$ are $C_{1-3}$ alkyl or taken together form an ethyl or propyl bridge; —$CH_2)_mOC(O)R^8$, wherein $R^8$ and m are as defined above, and —$(CH_2)_mC(O)OR^8$, wherein $R^8$ and m are as defined above.

Another embodiment of the present invention is directed to an antibody raised against a compound above wherein a sirolimus compound such as, e.g., rapamycin, is linked to an immunogenic carrier.

Another embodiment of the present invention is a polyclonal antibody raised against a compound comprising a moiety, such as a poly(amino acid) immunogenic carrier or a non-poly(amino acid) immunogenic carrier, linked to a sirolimus compound at position 32.

Another embodiment of the present invention is a kit comprising an antibody as mentioned above and a label conjugate of a sirolimus compound such as, e.g., rapamycin.

Another embodiment of the present invention is a kit comprising an antibody for a sirolimus compound such as, e.g., rapamycin, and a compound as mentioned above wherein a label is linked to a sirolimus compound such as, e.g., rapamycin.

Another embodiment of the present invention is a method for the detection of sirolimus compounds in a sample suspected of containing one or more of such compounds. The method comprises combining a sample with one or more compounds in accordance with embodiments of the present invention or with components of a kit such as mentioned above and examining the medium for the presence of a complex comprising the sirolimus compound and the antibody for sirolimus, the presence thereof indicating the presence of the sirolimus compound in the sample.

DETAILED DESCRIPTION OF SPECIFIC EMBODIMENTS

Figure 1:
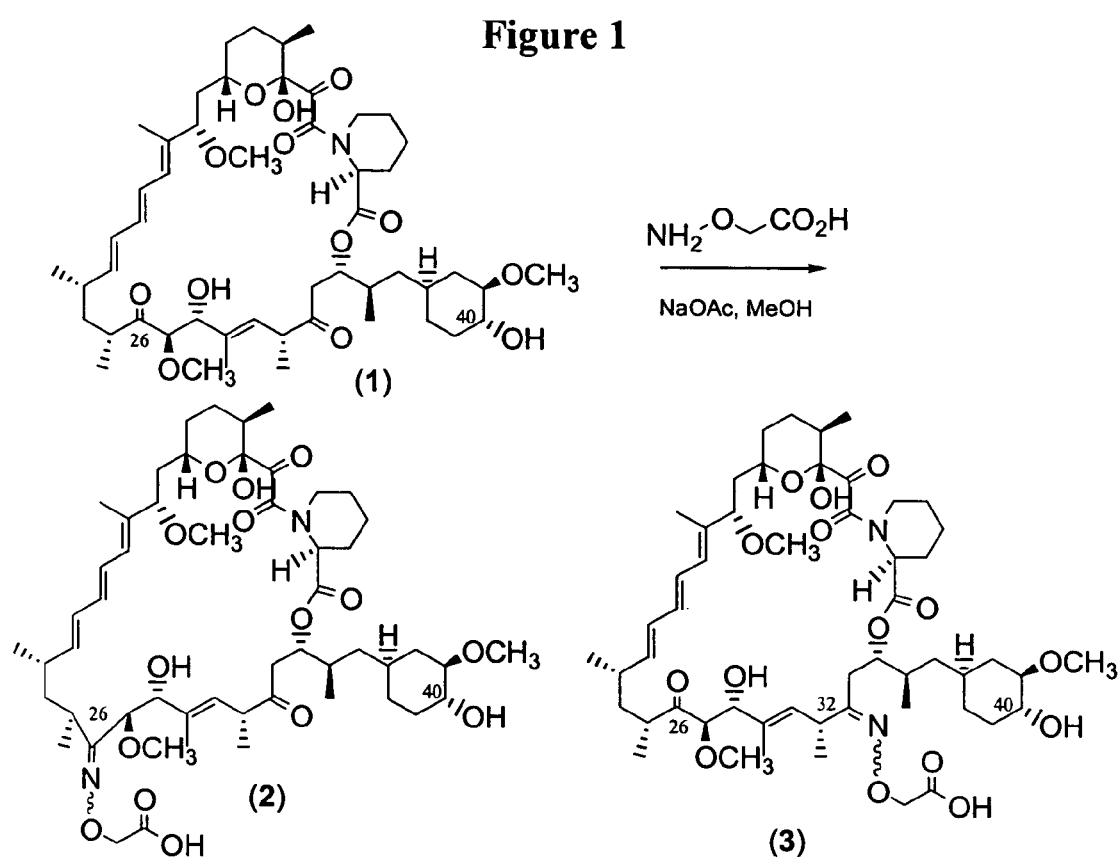
FIG. 1 is a scheme depicting the synthesis of oxime derivatives of sirolimus compounds at positions 26 and 32, respectively.

As mentioned above, an embodiment of the present invention is a compound comprising a moiety, such as a poly(amino acid), a non-poly(amino acid) label moiety, or a non-poly(amino acid) immunogenic carrier, linked to a sirolimus compound at position 26. Another embodiment of the present invention is a polyclonal antibody raised against a compound comprising a moiety, such as a poly(amino acid) or non-poly(amino acid) immunogenic carrier, linked to a sirolimus compound at position 32. These and other embodiments are discussed in more detail below. The present invention permits effective screening of samples for the presence of a sirolimus compound.

The term "sirolimus compound" as used herein includes rapamycin and its derivatives, other members of the sirolimus family and their derivatives, including, for example, esters, amides, haloacetamides, imides, and the like at one or more positions. Rapamycin derivatives include compounds containing a rapamycin nucleus, metabolites of rapamycin, and ring-opened rapamycin compounds. In some approaches, rapamycin derivatives are prepared through esterification of one or more hydroxyl groups into a carboxylic ester, a carbamate, a sulfonate ester, an amide, or the like. Rapamycin derivatives also include compounds resulting from the reduction of one or more carbonyl carbons to a hydroxyl group or reduction of one or more of the double bonds.

In some embodiments, immunogens comprising immunogenic carriers, including poly(amino acid) and non-poly(amino acid) immunogenic carriers, linked to a sirolimus compound such as, e.g., rapamycin, are synthesized and used to prepare antibodies specific for a sirolimus compound such as, e.g., rapamycin. The antibodies may be used in methods for detecting the sirolimus compounds in samples suspected of containing the drugs. In some embodiments, label conjugates, including poly(amino acid) and non-poly(amino acid) label conjugates, are prepared and may be employed in the above methods.

In some embodiments, the moiety may be linked to the sirolimus compound such as, e.g., rapamycin, at position 26 by means of a bond or a linking group. The linking group may comprise about 2 to about 50 atoms, or 4 to about 30 atoms, not counting hydrogen and may comprise a chain of from 2 to about 30 atoms, or 3 to about 20 atoms, each independently selected from the group normally consisting of carbon, oxygen, sulfur, nitrogen, and phosphorous. Part or all of the linking group may be a portion of the molecule being linked to the sirolimus compound such as, for example, an amino acid residue on a poly(amino acid) and the like. In some embodiments, the linking group comprises an oxime functionality.

The number of heteroatoms in the linking groups will normally range from about 0 to about 20, 1 to about 15, or about 2 to about 10. The linking groups may be aliphatic or aromatic. When heteroatoms are present, oxygen is normally present as oxo or oxy, bonded to carbon, sulfur, nitrogen or phosphorous, nitrogen is normally present as nitro, nitroso or amino, normally bonded to carbon, oxygen, sulfur or phosphorous; sulfur is analogous to oxygen; while phosphorous is bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters. One specific embodiment of a linking group comprising heteroatoms is an oxime functionality as mentioned above.

For the most part, when a linking group has a linking functionality (functionality for reaction with a moiety) such as, for example, a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities are linked to amine groups, carboxyl groups, active olefins, alkylating agents, e.g., bromoacetyl. Where an amine and carboxylic acid or its nitrogen derivative or phosphoric acid are linked, amides, amidines and phosphoramides are formed. Where mercaptan and activated olefin are linked, thioethers are formed. Where a mercaptan and an alkylating agent are linked, thioethers are formed. Where aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed. Various linking groups are well known in the art; see, for example, Cautrecasas, *J. Biol. Chem.* (1970) 245:3059.

In some embodiments, the moiety may be linked to the sirolimus compound such as, e.g., rapamycin, at position 32 by means of a linking group, which may comprise, for example, an oxime functionality, and polyclonal antibodies are raised against such sirolimus compounds.

As mentioned above, one of the attachable moieties is a poly(amino acid), which includes, among others, immunogenic proteins, label proteins, antibodies, and so forth. Various protein types are included within the term "poly (amino acid)," both natural and synthetic. These proteins include, for example, enzymes, albumins, serum proteins, e.g., globulins, lipoproteins, antibodies and the like. The molecular weight of the poly(amino acids) will generally be at least about 5,000 and have no upper limit, or about 10,000 to about 10,000,000, or about 15,000 to about 600,000. There will usually be different ranges depending on the type of protein involved. With label proteins such as, for example, enzymes, the range will be from about 10,000 to about 600,000, or from about 10,000 to about 300,000 molecular weight. There is usually at least about 1 sirolimus compound analog per about 200,000 molecular weight, or at least about 1 per about 150,000 molecular weight, or at least about 1 per about 100,000 molecular weight, or at least about 1 per about 50,000 molecular weight, and so forth. In the case of enzymes, the number of sirolimus compound analog groups is usually from 1 to about 20, about 2 to about 15, about 3 to about 12, or about 6 to about 10.

Enzymes of particular interest as label proteins are redox enzymes, particularly dehydrogenases such as glucose-6-phosphate dehydrogenase, lactate dehydrogenase, etc., and enzymes that involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations are known in the art. When a single enzyme is used as a label, other enzymes may find use such as hydrolases, transferases, and oxidoreductases, preferably hydrolases such as alkaline phosphatase and beta-galactosidase. Alternatively, luciferases may be used such as firefly luciferase and bacterial luciferase.

Illustrative co-enzymes that find use include NAD[H], NADP[H], pyridoxal phosphate, FAD[H], FMN[H], etc., usually coenzymes involving cycling reactions. See, for example, U.S. Pat. No. 4,318,980, the disclosure of which is incorporated herein by reference.

The term "non-poly(amino acid) labels" includes those labels that are not proteins (such as enzymes). The non-poly (amino acid) label is capable of being detected directly or is detectable through a specific binding reaction that produces a detectable signal. The non-poly(amino acid) labels include, for example, radioisotopes, luminescent compounds, supports, e.g., particles, plates, beads, etc., polynucleotides, and the like. More particularly, the label can be isotopic or non-isotopic, usually non-isotopic, and can be a polynucleotide coding for a catalyst, promoter, dye, coenzyme, enzyme substrate, radioactive group, a small organic molecule (including, e.g., biotin, fluorescent molecules, chemiluminescent molecules, and the like), amplifiable polynucleotide sequence, a support such as, for example, a particle such as latex or carbon particle or chromium dioxide (chrome) particle or the like, metal sol, crystallite, liposome, cell, etc., which may or may not be further labeled with a dye, catalyst or other detectable group, and the like.

The support may be comprised of an organic or inorganic, solid or fluid, water insoluble material, which may be transparent or partially transparent. The support can have any of a number of shapes, such as particle, including bead, film, membrane, tube, well, strip, rod, planar surfaces such as, e.g., plate, DENDRIMERS, and the like. Depending on the type of assay, the support may or may not be suspendable in the medium in which it is employed. Examples of suspendable supports are polymeric materials such as latex, lipid bilayers or liposomes, oil droplets, cells and hydrogels. Other support compositions include polymers, such as nitrocellulose, cellulose acetate, poly (vinyl chloride), polyacrylamide, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials.

A sirolimus compound derivative may be bound to a solid support in any manner known in the art, provided only that the binding does not substantially interfere with the derivatives ability to bind with an antibody. In some embodiments, the derivative may be coated or covalently bound directly to the solid phase or may have layers of one or more carrier molecules such as poly(amino acids) including proteins such as serum albumins or immunoglobulins, or polysaccharides (carbohydrates) such as, for example, dextran or dextran derivatives. Linking groups may also be used to covalently couple the solid support and the sirolimus compound. Other methods of binding the sirolimus compound derivatives are also possible. For instance, a solid support may have a coating of a binder for a small molecule such as, for example, avidin, an antibody, etc., and a small molecule such as, e.g., biotin, hapten, etc., can be bound to the sirolimus compound derivative or vice versa. The binding of components to the surface of a support may be direct or indirect, covalent or non-covalent and can be accomplished by well-known techniques, commonly available in the literature. See, for example, "Immobilized Enzymes," Ichiro Chibata, Halsted Press, New York (1978) and Cautrecasas, J. Biol. Chem., 245:3059 (1970). In some embodiments, the sirolimus compound is bound to a solid support by means of position 26 or position 32 and further by a linking group that comprises an oxime functionality.

The particles should have an average diameter of at least about 0.02 microns and not more than about 100 microns. In some embodiments, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus, E. coli,* viruses, and the like. The particles can also be particles comprised of organic and inorganic polymers, liposomes, latex particles, magnetic or non-magnetic, phospholipid vesicles, chylomicrons, lipoproteins, and the like. In some embodiments, the particles are chrome particles or latex particles.

The polymer particles can be formed of addition or condensation polymers. The particles will be readily dispersible in an aqueous medium and can be adsorptive or functionalizable so as to permit conjugation to a sirolimus compound, either directly or indirectly through a linking group. The particles can also be derived from naturally occurring materials, naturally occurring materials that are synthetically modified, and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like.

A poly(amino acid) label or a non-poly(amino acid) label may be a member of a signal producing system. The signal producing system may have one or more components, at least one component being the label, whether poly(amino acid) or non-poly(amino acid). The signal producing system generates a signal that relates to the presence of a sirolimus compound in a sample. The signal producing system includes all of the reagents required to produce a measurable signal. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. Exemplary signal-producing systems are described in U.S. Pat. No. 5,508,178 (Rose, et al.), the relevant disclosure of which is incorporated herein by reference.

Immunogenic carriers include certain poly(amino acids) and non-poly(amino acids). By the term "immunogenic carrier" is meant a group which, when conjugated to a hapten forms an immunogen that is injected into a mammal, induces an immune response and elicits the production of antibodies that bind to the hapten. Haptens are compounds capable of binding specifically to corresponding antibodies but do not themselves act as immunogens (or antigens) for preparation of the antibodies. Antibodies that recognize a hapten can be prepared against compounds comprised of the hapten linked to an immunogenic (or antigenic) carrier. Immunogenic carriers are also sometimes referred to as antigenic carriers. Typical immunogenic carriers include, without limitation, poly(amino acids), polysaccharides, nucleic acids and particles (biologic and synthetic materials). A wide variety of such carriers are disclosed in Davalian, et al., U.S. Pat. No. 5,089,390, column 4, line 57 to column 5, line 5, which is incorporated herein by reference.

The molecular weight range (in Daltons) for poly(amino acids) that are immunogenic carriers such as protein antigens is from about 5,000 to about 10,000,000, from about 20,000 to about 600,000, from about 25,000 to about 250,000 molecular weight. Poly(amino acid) immunogenic carriers include proteins such as, for example, albumins, serum proteins, e.g., globulins, ocular lens proteins and lipoproteins, and so forth. Illustrative proteins include bovine serum albumin (BSA), keyhole limpet hemocyanin ("KLH"), egg ovalbumin, bovine gamma-globulin (BGG), and the like. Non-poly(amino acid) immunogenic carriers include polysaccharides, particles, and the like.

As mentioned above, the immunogenic carrier may be a polysaccharide, which is a high molecular weight polymer of monosaccharides that may be prepared naturally or synthetically and usually involves repeated condensations of monosaccharides. Examples of polysaccharides are starches, glycogen, cellulose, carbohydrate gums, such as gum arabic, agar, and so forth. The polysaccharide can also contain poly(amino acid) residues and/or lipid residues.

The terms "non-label poly(amino acid) moieties" and "non-immunogenic carrier poly(amino acid) moieties" mean poly(amino acids) that are not normally considered labels or immunogenic carriers although such moieties may be labels or immunogenic carriers in certain circumstances. For example, an antibody may not be considered a label but may be a label if the antibody is modified to include a signal producing moiety or part of a signal producing system. Furthermore, an antibody may not be considered as an immunogenic carrier but is nonetheless capable of being an immunogenic carrier in certain circumstances because of it higher molecular weight.

In some embodiments the above conjugates have the structure:

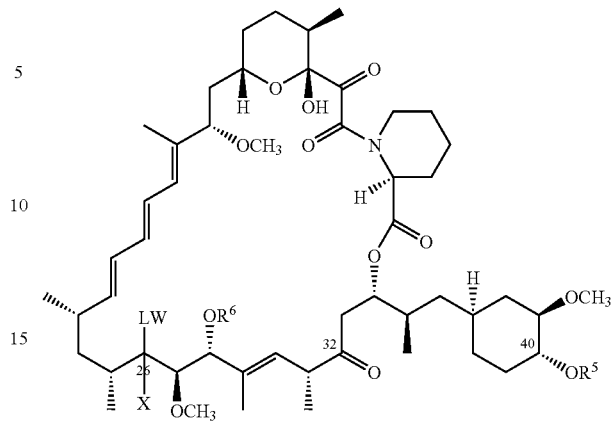

wherein L is a linking group, X is hydrogen, $R^5$ and $R^6$ are independently selected from hydrogen, $C_{1-7}$ alkyl, or $C(O)$ $C_{1-6}$ alkyl, and W is a moiety, selected from the group consisting of poly(amino acids), non-poly(amino acid) label moieties, and non-poly(amino acid) immunogenic carriers, or, in some embodiments, L is a linking group and W is a functionality for attachment to a poly(amino acid), a non-poly(amino acid) label moiety or a non-poly(amino acid) immunogenic carrier and the like. Such functionalities include, by way of illustration and not limitation, maleimides, succinimides, haloacetamides (bromoacetamide, iodoacetamide, chloroacetamide, and the like), and so forth. In some embodiments, L comprises an oxime functionality.

In some embodiments, the above conjugates have the structure:

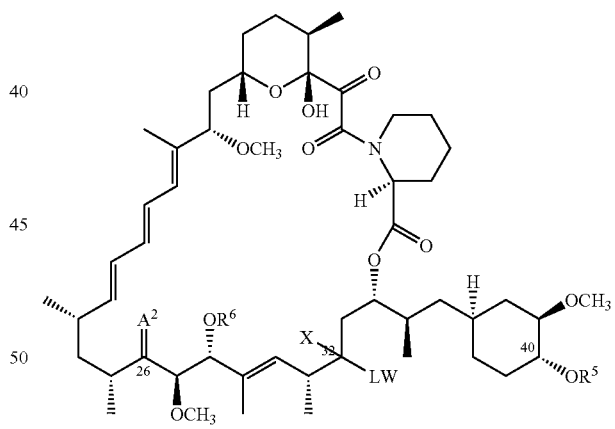

wherein L is a linking group, X is hydrogen, $R^5$ and $R^6$ are independently selected from hydrogen, $C_{1-7}$ alkyl, or $C(O)$ $C_{1-6}$ alkyl, and W is a moiety, selected from the group consisting of poly(amino acids), non-poly(amino acid) label moieties, and non-poly(amino acid) immunogenic carriers, or, in some embodiments, L is a linking group and W is a functionality for attachment to a poly(amino acid), a non-poly(amino acid) label moiety or a non-poly(amino acid) immunogenic carrier and the like. Such functionalities include, by way of illustration and not limitation, maleimides, succinimides, haloacetamides (bromoacetamide, iodoacetamide, chloroacetamide, and the like), and so forth.

Some embodiments of the present invention are directed to polyclonal antibodies raised against a compound of the above structure wherein W is a poly(amino acid) or non-poly(amino acid) immunogenic carrier. In some embodiments, the polyclonal antibodies are raised against a compound of the above structure wherein L comprises an oxime functionality.

Some embodiments of the present invention are directed to compounds of structure I:

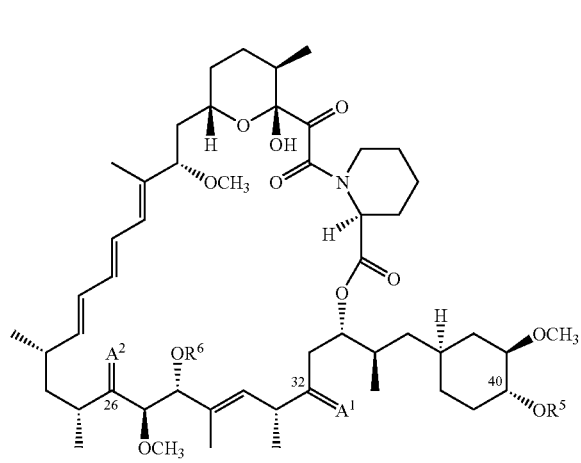

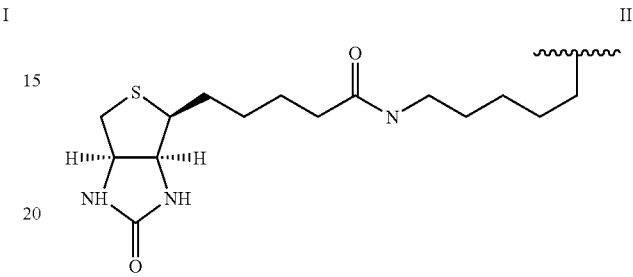

wherein, when $A^1$ is not oxo, then in some embodiments at least one or more of m is 1, or t is 1, or y is 1 to about 5, or v is 1 to about 12, or x is 1, or z is 1, and in some embodiments of the above embodiments n is also at least 1; or, when $A^1$ is not oxo, then $R^1$ is II, $R^1$ is a moiety, such as a poly(amino acid), a non-poly (amino acid) label moiety, or a non-poly(amino acid) immunogenic carrier, or a functionality, as mentioned above, for linking to a poly(amino acid), a non-poly(amino acid) label moiety, or a non-poly(amino acid) immunogenic carrier, or and in some embodiments, when $A^1$ is not oxo, then m is 1, or $R^1$ is II, and wherein any $R^1$ group may be linked through a moiety such as, for example, an amino group, and the like including by way of illustration an amino group of a protein, an amino group introduced into a polysaccharide such as, e.g., aminodextran, and so forth, $R^2$ and $R^3$ are independently selected from hydrogen, $C_{1-10}$ alkyl, benzyl, OH, halogen, $C_{1-6}$ alkoxy; $C_{3-10}$ alkenyl, and $C_{3-10}$ alkynyl, wherein $A^1$ and $A^2$ are independently oxo or a group of the formula Ia:

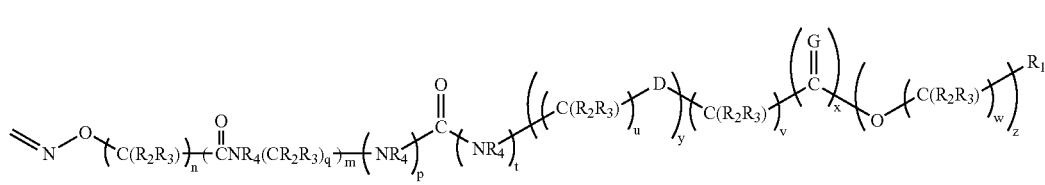

with the proviso that both $A^1$ and $A^2$ cannot be oxo and wherein:

D is O or S,
G is O or $NR^2$,
n, q, u, v and w are independently 0 to about 12, 0 to about 11, 0 to about 10, 0 to about 9, 0 to about 8, 0 to about 7, 0 to about 6, 0 to about 5, 0 to about 4, 0 to about 3, 0 to about 2, 0 to 1, 1 to about 12, 1 to about 11, 1 to about 10, 1 to about 9, 1 to about 8, 1 to about 7, 1 to about 6, 1 to about 5, 1 to about 4, 1 to about 3, 1 to 2, about 2 to about 10, about 2 to about 8, about 2 to about 6, about 2 to about 5, about 2 to about 4, about 2 to about 3, about 3 to about 8, about 3 to about 6, about 3 to about 5, about 3 to about 4, about 4 to about 6, about 4 to about 5, and so forth,
m is 0 or 1,
p is 0 or 1,
t is 0 or 1,
y is 0 to about 5, 0 to about 4, 0 to about 3, 0 to about 2, 0 to 1, 1 to about 5, 1 to about 4, 1 to about 3, 1 to about 2, about 2 to about 5, about 2 to about 4, about 3 to about 4, about 3 to about 5, about 4 to about 5,
x is 0 or 1,
z is 0 or 1, $R^4$ is independently hydrogen, $C_{1-10}$ alkyl, benzyl, $C_{3-10}$ alkenyl, $C_{3-10}$ alkynyl; and $R^5$ and $R^6$ are independently selected from hydrogen; phenyl; substituted phenyl in which the substituents are X, Y and Z; 1- or 2-naphthyl; substituted 1- or 2-naphthyl in which the substituents are X, Y and Z; $C(O)C_{1-6}$ alkyl; $C_{1-10}$ alkyl; $C_3$–$C_{10}$ cycloalkyl; substituted $C_{1-10}$ alkyl in which one or more substituent(s) is(are) selected from hydroxy, oxo, $C_{1-6}$-alkoxy; phenyl, substituted phenyl in which the substituents on phenyl are X, Y and Z and $OC(O)C_{1-6}$ alkyl; $C_{3-10}$ alkenyl; $C_{4-10}$ cycloalkenyl; substituted $C_{3-10}$ alkenyl in which one or more substituent(s) is(are) selected from hydroxy, oxo, $C_{1-6}$-alkoxy, phenyl, substituted phenyl in which the substituents on phenyl are X, Y and Z and $OC(O)C_{1-6}$ alkyl; $C_{3-10}$ alkynyl; and substituted $C_{3-10}$ alkynyl in which one or more substituent(s) is(are) selected from hydroxy, oxo, $C_{1-6}$-alkoxy, phenyl, substituted phenyl, in which the substituents on phenyl are X, Y and Z and $OC(O)C_{1-6}$ alkyl;

X, Y and Z are independently selected from: hydrogen; $C_{1-7}$ alkyl; $C_{2-6}$ alkenyl; halogen (including fluorine, bromine, chlorine and iodine); CN; C(O)H; perhalosubstituted (including fluoro, bromo, chloro and iodo) groups such as $CF_3$; $SR^7$, wherein $R^7$ is hydrogen, $C_{1-6}$ alkyl, $CF_3$ or phenyl; $SOR^7$, wherein $R^7$ is as defined above; $SO_2R^7$, wherein $R^7$ is as defined above; $CONR^5 R^6$, wherein $R^5$ and $R^6$ are as defined above; $-(CH_2)_rOR^8$, wherein $R^8$ is hydrogen, $C_{1-3}$ alkyl; hydroxy-$C_{2-3}$ alkyl, and r is 0–2; $C_{1-3}$ alkyl; hydroxy-$C_{2-3}$ alkyl; $CH(OR^9)(OR^{10})$, wherein $R^9$ and $R^{10}$ are $C_{1-3}$ alkyl or taken together form an ethyl or propyl bridge; $-(CH_2)_rOC(O)R^8$, wherein $R^8$ and r are as defined above, and $-(CH_2)_rC(O)OR^8$ wherein $R^8$ and r are as defined above.

The phrase "at least" as used herein means that the number of specified items may be equal to or greater than the number recited. The phrase "about" as used herein means that the number recited may differ by plus or minus 20%; for example, "about 5" means a range of 4 to 6.

In some embodiments of the above, $A^1$ and $A^2$ are independently oxo or a group of the formula Ib:

with the proviso that both $A^1$ and $A^2$ cannot be oxo and wherein:

n is 0 to about 12, 0 to about 1, 0 to about 10, 0 to about 9, 0 to about 8, 0 to about 7, 0 to about 6, 0 to about 5, 0 to about 4, 0 to about 3, 0 to about 2, 0 to 1, 1 to about 12, 1 to about 11, 1 to about 10, 1 to about 9, 1 to about 8, 1 to about 7, 1 to about 6, 1 to about 5, 1 to about 4, 1 to about 3, 1 to 2, about 2 to about 10, about 2 to about 8, about 2 to about 6, about 2 to about 5, about 2 to about 4, about 2 to about 3, about 3 to about 8, about 3 to about 6, about 3 to about 5, about 3 to about 4, about 4 to about 6, about 4 to about 5, and so forth, m is 0 or 1, p is 0 or 1, q is 0 to about 12, 0 to about 11, 0 to about 10, 0 to about 9, 0 to about 8, 0 to about 7, 0 to about 6, 0 to about 5, 0 to about 4, 0 to about 3, 0 to about 2, 0 to 1, 1 to about 12, 1 to about 11, 1 to about 10, 1 to about 9, 1 to about 8, 1 to about 7, 1 to about 6, 1 to about 5, 1 to about 4, 1 to about 3, 1 to 2, about 2 to about 10, about 2 to about 8, about 2 to about 6, about 2 to about 5, about 2 to about 4, about 2 to about 3, about 3 to about 8, about 3 to about 6, about 3 to about 5, about 3 to about 4, about 4 to about 6, about 4 to about 5, and so forth, and wherein, when $A^1$ is not oxo, then in some embodiments m is 1 and in some embodiments of those embodiments p is 1 or n is at least 1; or when $A^1$ is not oxo, then $R^1$ is II, $R^1$ to $R^6$ and X, Y and Z and other terms not specifically defined here are as defined above and wherein any $R^1$ group may be linked through a moiety of $R^1$ such as, for example, an amino group, and the like including by way of illustration an amino group of a protein, an amino group introduced into a polysaccharide such as, e.g., aminodextran, and so forth.

In some embodiments of the above, $A^1$ is oxo and the remaining groups are as defined above.

In some embodiments of the above, $A^1$ and $A^2$ are independently oxo or a group of the formula Ic:

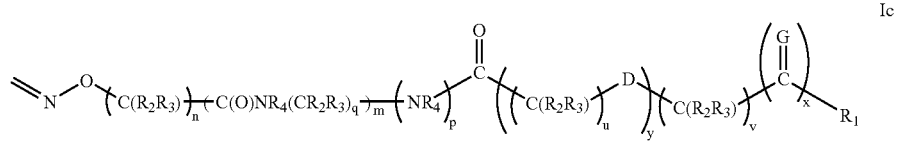

with the proviso that both $A^1$ and $A^2$ cannot be oxo and wherein:

D is O or S,

G is O or $NR^2$, n, q, u, and v are independently 0 to about 12, 0 to about 11, 0 to about 10, 0 to about 9, 0 to about 8, 0 to about 7, 0 to about 6, 0 to about 5, 0 to about 4, 0 to about 3, 0 to about 2, 0 to 1, 1 to about 12, 1 to about 11, 1 to about 10, 1 to about 9, 1 to about 8, 1 to about 7, 1 to about 6, 1 to about 5, 1 to about 4, 1 to about 3, 1 to 2, about 2 to about 10, about 2 to about 8, about 2 to about 6, about 2 to about 5, about 2 to about 4, about 2 to about 3, about 3 to about 8, about 3 to about 6, about 3 to about 5, about 3 to about 4, about 4 to about 6, about 4 to about 5, and so forth, m is 0 or 1, p is 0 or 1, y is 0 to about 5, 0 to about 4, 0 to about 3, 0 to about 2, 0 to 1, 1 to about 5, 1 to about 4, 1 to about 3, 1 to about 2, about 2 to about 5, about 2 to about 4, about 3 to about 4, about 3 to about 5, about 4 to about 5, x is 0 or 1, z is 0 or 1, and wherein, when $A^1$ is not oxo, then in some embodiments at least one of m is 1, or t is 1, or y is 1 to about 5, or v is 1 to about 12, or x is 1, and in some embodiments of those embodiments n is at least 1; or, when $A^1$ is not oxo, then $R^1$ is A, and wherein in some embodiments $A^1$ is oxo, $R^1$ to $R^6$ and X, Y and Z and other terms not specifically defined here are as defined above and wherein any $R^1$ group may be linked through a moiety of $R^1$ such as, for example, an amino group, and the like including by way of illustration an amino group of a protein, an amino group introduced into a polysaccharide such as, e.g., aminodextran, and so forth.

In a specific embodiment, the group of the formula Ic is:

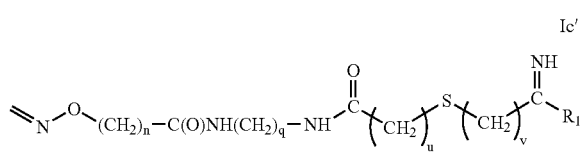

and includes imine salts thereof such as, for example, imine salt of mineral acids, e.g., HCl. In other specific embodiments of the above group of formula Ic', n, q, u and v are 1.

In some embodiments of the above, $A^1$ and $A^2$ are independently oxo or a group of the formula Id:

Id with the proviso that both $A^1$ and $A^2$ cannot be oxo and wherein:

D is O or S, n, u, and v are independently 0 to about 12, 0 to about 11, 0 to about 10, 0 to about 9, 0 to about 8, 0 to about 7, 0 to about 6, 0 to about 5, 0 to about 4, 0 to about 3, 0 to about 2, 0 to 1, 1 to about 12, 1 to about 11, 1 to about 10, 1 to about 9, 1 to about 8, 1 to about 7, 1 to about 6, 1 to about 5, 1 to about 4, 1 to about 3, 1 to 2, about 2 to about 10, about 2 to 3 to about 8, about 3 to about 6, about 3 to about 5, about 3 to about 4, about 4 to about 6, about 4 to about 5, and so forth, t is 0 or 1, y is 0 to about 5, 0 to about 4, 0 to about 3, 0 to about 2, 0 to 1, 1 to about 5, 1 to about 4, 1 to about 3, 1 to about 2, about 2 to about 5, about 2 to about 4, about 3 to about 4, about 3 to about 5, about 4 to about 5, wherein, when $A^1$ is not oxo, then in some embodiments at least one of t is 1, or y is 1 to about 5, or v is 1 to about 12, and in some embodiments of those embodiments, n is at least 1; or, when $A^1$ is not oxo, then $R^1$ is II, and wherein in some embodiments $A^1$ is oxo, $R^1$ to $R^6$ and X, Y and Z and other terms not specifically defined here are as defined above and wherein any $R^1$ group may be linked through a moiety of $R^1$ such as, for example, an amino group, and the like including by way of illustration an amino group of a protein, an amino group introduced into a polysaccharide such as, e.g., aminodextran, and so forth. In some embodiments the polysaccharide such as, e.g., aminodextran may be bound to a particle such as, e.g., a chromium dioxide particle, and the like.

In a specific embodiment of the above group Id, n is 1, t is 1, u is 2, y is 2 and v is 1.

A specific embodiment of group Id is:

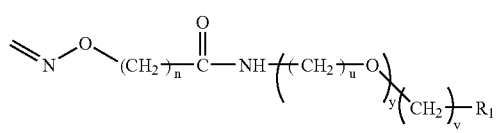

Id' wherein n is 1, u is 2, y is 2 and v is 1 and wherein any $R^1$ group may be linked through a moiety of $R^1$ such as, for example, an amino group, and the like including by way of illustration an amino group of a protein, an amino group introduced into a polysaccharide such as, e.g., aminodextran, and so forth.

The compounds of the invention have asymmetric centers and this invention includes all of the optical isomers and mixtures thereof. In addition, compounds with carbon-carbon double bonds may occur in Z- and E- forms with all isomeric forms of the compounds being included in the present invention. Where appropriate, the isomers/stereoisomers can be separated by procedures known in the art and used individually.

When any variable (e.g., alkyl, aryl, $R^1$, $R^2$, $R^3$, etc.) occurs more than one time in Structure I, its definition on each occurrence is independent of the other. For example, a compound of the invention includes Structure I wherein in each occurrence of $R^2$ the same or different $R^2$ may be present.

Another embodiment of the invention includes the compounds of Structure I wherein $R^5$ and $R^6$ are independently selected from hydrogen, $C_{1-7}$ alkyl, or $C(O)C_{1-6}$ alkyl, preferably hydrogen; $A^2$ is oxo; and $A^1$ is represented by a group of the formula Ia, wherein $R^2$ and $R^3$ are hydrogen and n is about 1 to about 12, about 6 to about 12, about 6 to about 9, m is 1, and p is 0 or 1.

Another embodiment of the invention includes the compounds of Structure I wherein $R^5$ and $R^6$ are independently selected from hydrogen, $C_{1-7}$ alkyl, or $C(O)C_{1-6}$ alkyl, preferably hydrogen; $A^1$ is oxo; and $A^2$ is represented by a group of the formula Ia, wherein $R^2$ and $R^3$ are hydrogen and n is about 1 to about 12, about 6 to about 12, about 6 to about 9, m is 0, p is 1; $R^4$ is hydrogen or $C_{1-4}$ alkyl, preferably hydrogen.

Another embodiment of the invention includes the compounds of Structure I wherein $R^5$ and $R^6$ are independently selected from hydrogen, $C_{1-7}$ alkyl, or $C(O)C_{1-6}$ alkyl, preferably hydrogen; $A^1$ is oxo; and A is represented by formula Ia, wherein $R^2$ and $R^3$ are hydrogen and n is about 1 to about 12, about 1 to about 9, about 1 to about 6, about 1 to about 3, or 1, m is 1, q is about 1 to about 9, about 1 to about 6, about 1 to about 3, or 1, and p is 1.

Another embodiment of the invention includes the compounds of Structure I wherein $R^5$ and $R^6$ are independently selected from hydrogen, $C_{1-7}$ alkyl, or $C(O)C_{1-6}$ alkyl, preferably hydrogen; $A^1$ is oxo; and $A^2$ is represented by formula Ia, wherein $R^2$ and $R^3$ are hydrogen and n is about 1 to about 12, about 6 to about 12, about 6 to about 9, m is 1, q is 1 to about 12, 2 to about 6, about 2, p is 0.

Another embodiment of the invention includes the compounds of Structure I wherein $R^5$ and $R^6$ are independently selected from hydrogen, $C_{1-7}$ alkyl, or $C(Q)C_{1-6}$ alkyl, preferably hydrogen; $A^2$ is oxo; and $A^1$ is represented by a group of the formula Ia, wherein $R^2$ and $R^3$ are hydrogen and n is about 1 to about 12, about 6 to about 12, about 6 to about 9, m is 0 or 1, and p is 0 or 1, and $R^1$ is II.

Another embodiment of the invention includes the compounds of Structure I: wherein $R^1$ and $R^2$ are independently selected from hydrogen, $C_{1-7}$ alkyl, or $C(O)C_{1-6}$ alkyl, preferably hydrogen; $A^1$ is oxo; and $A^2$ is represented by formula Ia, wherein $R^2$ and $R^3$ are hydrogen and n is about 1 to about 12, about 6 to about 12, about 6 to about 9, m is 0, p is 0; and $R^4$ is hydrogen or $C_{1-4}$ alkyl.

Some embodiments of the present invention are directed to compounds of structure III:

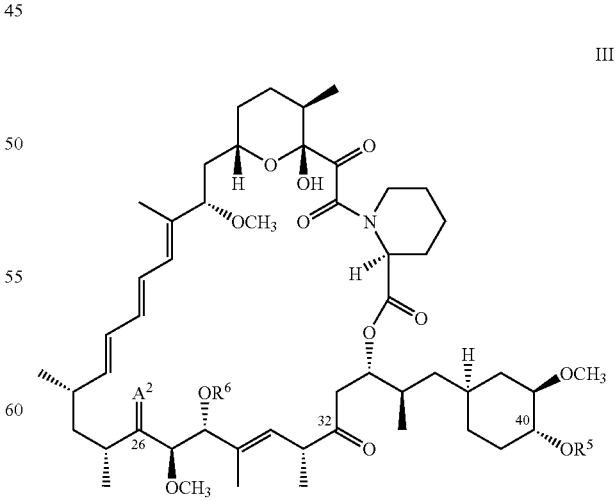

III wherein $A^2$ is a group of the formula Ia above or a group of formula Ib above or a group of the formula Ic above or a group of the formula Id above and embodiments thereof as specifically identified above and excluding embodiments identified for $A^1$ not being oxo.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. The term "alkenyl" includes hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable. The term "alkynyl" refers to a straight or branched chain hydrocarbon of a specified number of carbon atoms containing at least one carbon-carbon triple bond, including ethynyl, 1-propynyl, 2-propynyl, 1-butynyl, and 2-butynyl. The term "alkoxy" includes alkyl groups of a designated number of carbon atoms of either a straight, branched or cyclic configuration wherein the alkyl group includes an ether oxygen for linking to the parent compound. The term "halogen" includes fluoro, chloro, bromo and iodo.

As mentioned above, the sirolimus compound may be bound to a particle. In some embodiments a particle may be bound to a protein that is linked to the sirolimus compound as discussed above, for example, as shown in structure I with a linking group of the formula Ia. In some embodiments an amine group of the protein may be conjugated to the particle by means of a linking group of the formula where $R^2$ and $R^3$ are as defined above:

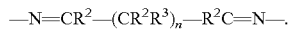

$$-N=CR^2-(CR^2R^3)_n-R^2C=N-.$$

For example, in some embodiments the sirolimus compound bound to the particle may have the general formula where $R^2$ and $R^3$ are as defined above:

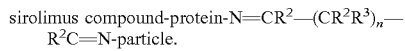

sirolimus compound-protein-$N=CR^2-(CR^2R^3)_n-$
   $R^2C=N$-particle.

In some embodiments a particle may be bound to a polysaccharide as discussed above where the polysaccharide is linked to the sirolimus compound, for example, as shown in structure I with a linking group of the formula Ia. For example, in some embodiments the sirolimus compound bound to the particle may have the formula:

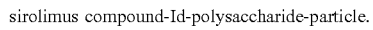

sirolimus compound-Id-polysaccharide-particle.

The synthesis of representative examples of the above compounds is discussed herein by way of illustration and not limitation. Other synthetic procedures will be suggested to those skilled in the art in view of the disclosure herein. Other compounds within the scope of the present invention may be prepared using suitable variants of the reagents employed below.

The oxime group can be added to rapamycin or its derivatives in the presence of a mild base such as sodium acetate (NaOAc). The preferred solvent for the reaction is methanol/water. In most cases, the C-26 and C-32 oxime acid compounds can be formed in a single preparative step. These compounds can then be separated using preparative thin-layer chromatography (TLC). However, it is not always necessary to perform the separation. A combination of the C-26 and C-32 may be used for simplicity of manufacture.

The oxime acid compound may be activated by an appropriate activating agent such as, for example, dicyclohexylcarbodiimide (DCC) and N-hydroxysuccinic acid ester (NHS), EDAC and so forth in an organic solvent such as, for example, an ether, e.g., tetrahydrofuran, 18-crown-6, and so forth, and combinations thereof. The resulting activated compound is then reacted with the amine group of a protein such as, for example, KLH, BSA, BGG and the like in an aqueous buffered medium such as, e.g., phosphate buffered saline, and so forth, to give protein-rapamycin conjugates.

Alternatively, the resulting activated compound may be reacted with the amine group of a linking moiety. For example, the resulting activated compound may be reacted with an alkylene diamine, e.g., ethylene diamine, wherein one of the amine groups is in the form of an amide of a halogenated $C_1-C_{10}$ carboxylic acid such as, for example, bromoacetic acid, etc., and the other amine group is in the form of a hydrobromide. The reaction may be carried out in an organic solvent such as, for example, a halogenated hydrocarbon, e.g., methylene chloride in the presence of an organic base such as a mono-, di-, and tri-alkylamine, for example, diisopropylethylamine (DIPEA). Other suitable bases include ethylamine, diethylamine, triethylamine and so forth. The resulting product has a terminal bromoalkylene that may be reacted with a thiol functionality that is present in or introduced into the moiety to be linked. For example, a thiol group may be introduced into a protein by reaction with, for example, 2-iminothiolane hydrochloride and the like. The medium is usually a buffered medium such as, for example, aqueous phosphate buffered medium and the like. The conjugation to the protein may be conducted in an organic solvent such as, for example, dimethylformamide (DMF), ethers, and the like to give protein-rapamycin conjugates.

Rapamycin conjugates to solid surfaces or supports such as, for example, particles, may be carried out by reacting activated oxime acid compounds with a protein such as, for example, an immunoglobulin, in a buffered aqueous medium such as, e.g., phosphate buffered saline at about neutral pH. A particle such as, for example, a chrome particle or the like, is derivatized with a suitable linking moiety such as, for example, a linking moiety obtained by reacting an amino group on the particle with a dialdehyde such as, for example, glutaraldehyde and the like. This particle compound in combination with the immunoglobulin reagent yields the desired particle-rapamycin conjugate.

Alternatively, rapamycin conjugates to solid surfaces or supports such as, e.g., particles, may be carried out by reacting activated oxime acid compounds with a dextran derivative. For example, an amino group of a particle such as, e.g., a chrome particle, may be reacted with a functionalized dextran such as, e.g., dextran aldehyde. The reaction is conducted in the presence of a reducing agent such as, for example, NaCNBH$_3$, and the like in an aqueous buffered medium such as, e.g., phosphate buffered saline at a pH of about 6. The functionalized dextran-particle conjugate is then reacted with activated oxime acid compounds to give the desired rapamycin-particle conjugates.

Other approaches to preparing compounds in accordance with embodiments of the present invention will be suggested to those skilled in the art in view of the disclosure herein.

Enzyme conjugates may be prepared from compounds in accordance with the present invention. In general, functional groups suitable for attaching the compound to the enzyme are usually an activated ester or alkylating agent when the amino acid(s) that are to be conjugated on the enzyme have amino or hydroxyl groups and are usually alkylating agents or the like when the amino acid(s) that are to be conjugated on the enzyme comprise a sulfur atom such as, e.g., a cysteine. A large number of suitable functional groups are available for attaching to amino groups and alcohols such as activated esters including imidic esters, sulfonic esters and phosphate esters, activated nitrites, aldehydes, ketones, alkylating agents and the like. Conjugation of haptens to proteins using these and other attaching groups are well known in the art and are described in reviews such as for example, Maggio, E. T. "Enzyme-Immunoassay" (CRC Press, Boca Raton, Fla., 1980), Chapter 4, which contains an assortment of conjugation techniques; pages 81–88 of which are incorporated herein by reference. These techniques may be employed to link the present sirolimus compounds (haptens) to enzymes to form enzyme-sirolimus compound conjugates.

Following reaction of the enzyme with a compound such as discussed above to form a conjugate, the product is then optionally purified as may be required. The purification and characterization of poly(amino acid)-hapten conjugates, in general, has been described in detail Maggio, et al.; "enzyme-immunoassay" (CRC Press, Boca Raton, Fla., 1980), Chapter 4, pages 86–88 of which are incorporated herein by reference. For example, if the conjugate is a mutant G6PDH-hapten conjugate, the purification can be by dialysis against aqueous/organic and aqueous solutions such as water/DMF (dimethylformamide) or water, or by gel filtration chromatography on supports such as Sephadex, and the like.

As mentioned above, the conjugation can involve binding of a hapten to a free thiol group present on an amino acid side chain of the enzyme (e.g. cysteine). Such conjugation involves alkylation of the thiol sulfur atom by treatment with an electrophilic compound such as an alpha- or beta-unsaturated amide, ketone, ester, or the like, or an alkylating agent such as a reactive halide, e.g., bromide, or sulfonate or the like or reaction with an active disulfide such as a 2-nitro-4-carboxyphenyl disulfide. Specific examples by way of illustration and not limitation include alpha-bromoamides, maleimides, vinyl sulfones, alpha-iodoketones, and the like. The electrophilic compound in the present circumstance would be a sirolimus compound with a linking group having a functionality as discussed above for attachment to, for example, an enzyme.

Conjugation reactions with enzymes can be affected by a number of factors. These include, but are not confined to, pH, temperature, buffer, ionic strength, substances which may protect the enzyme active site, amount and type of cosolvent, reaction time, and activation chemistry. A range of pH values from about 5.0 to about 9.5 can usually be used for conjugation reactions. These reactions are generally carried out at about 0 to about 40 degrees C., preferably about 4 to about 20 degrees C.

A number of buffers and salts, both alone and in combination, can be used for such reactions. These include Tris, bicarbonate, phosphate, pyrophosphate, ethylenediamine tetraacetate (EDTA), KCl, NaCl, and many others. The active site may be protected by substrates (i.e. glucose-6-phosphate for glucose-6-phosphate dehydrogenase), cofactors ($NAD^+$, NADH, $NADP^+$, NADPH) and cofactor analogs (thio-$NAD^+$, thio-NADH, thio-$NADP^+$, or thio-NADPH), and compounds that react reversibly with lysine (i.e. pyridoxal) to reduce deactivation of the enzyme during conjugation.

Cosolvents which may enhance solubility of the sirolimus compound include, but are not limited to, dimethylformamide, carbitol, dimethyl sulfoxide, 1-methyl-2-pyrrolidinone, and 1,3-dimethyl-3,4,5,6-tetrahydro 2(1H)-pyrimidinone. These may be useful at about 1 to about 30% of the reaction volume. Reactions can vary from about 15 minutes to many days, depending on the activation chemistry. Carboxylic compounds may be activated to form esters with N-Hydroxysuccinimide or its sulfo-analog, or to mixed anhydrides through reaction with carbitol chloroformate or t-butylchloroformate, or may be coupled directly using carbodiimides such as 1-ethyl-3-(3-dimethylaminopropyl) carbodiimide hydrochloride (EDAC). For reaction with cysteine thiols on the enzyme, the sirolimus compound should contain a good leaving group such as I, Br or tosyl; alternatively, the hapten can contain a thiol, preferably activated with 2,2' dithiodipyridine or 5,5'-dithio-bis(2-nitrobenzoic acid) (DTNB).

Another method of conjugation, described in Rowley, G. L., D. Leung, and P. Singh (U.S. Pat. No. 4,220,722) involves modification of the enzyme with bromoacetyl containing reactants; the bromo groups are subsequently reacted with thiol-containing haptens. The reaction of enzyme with bromoacetyl modifier, and the bromoacetyl enzyme with the thiolated hapten, are subject to the same reaction condition variables described above.

Any of the compounds discussed above may be purified by known techniques such as, for example, dialysis, chromatography, and combinations thereof.

The immunogenic conjugates of the present invention are employed to prepare antibodies for a sirolimus compound for the detection of a sirolimus compound in a sample suspected of containing the same. The antibodies specific for a sirolimus compound for use in immunoassays can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Antiserum containing antibodies (polyclonal) is obtained by well-established techniques involving immunization of an animal, such as a rabbit, guinea pig, or goat, with an appropriate immunogen and obtaining antisera from the blood of the immunized animal after an appropriate waiting period. State-of-the-art reviews are provided by Parker, Radioimmunoassay of Biologically Active Compounds, Prentice-Hall (Englewood Cliffs, N.J., U.S., 1976), Butler, J. Immunol. Meth. 7: 1–24 (1975); Broughton and Strong, Clin. Chem. 22: 726–732 (1976); and Playfair, et al., Br. Med. Bull. 30: 24–31 (1974).

Antibodies can also be obtained by somatic cell hybridization techniques, such antibodies being commonly referred to as monoclonal antibodies. Monoclonal antibodies may be produced according to the standard techniques of Köhler and Milstein, *Nature* 265:495–497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3–46 (1981). Samples of an appropriate immunogen preparation are injected into an animal such as a mouse and, after a sufficient time, the animal is sacrificed and spleen cells obtained.

Alternatively, the spleen cells of a non-immunized animal can be sensitized to the immunogen in vitro. The spleen cell chromosomes encoding the base sequences for the desired immunoglobulins can be compressed by fusing the spleen cells, generally in the presence of a non-ionic detergent, for example, polyethylene glycol, with a myeloma cell line. The resulting cells, which include fused hybridomas, are allowed to grow in a selective medium, such as HAT-medium, and the surviving immortalized cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Alternatively, the cell producing the desired antibody can be grown in a hollow fiber cell culture device or a spinner flask device, both of which are well known in the art. Various conventional ways exist for isolation and purification of the monoclonal antibodies from other proteins and other contaminants (see Köhler and Milstein, supra).

In another approach for the preparation of antibodies the sequence coding for antibody binding sites can be excised from the chromosome DNA and inserted into a cloning vector, which can be expressed in bacteria to produce recombinant proteins having the corresponding antibody binding sites.

In general, antibodies can be purified by known techniques such as chromatography, e.g., DEAE chromatography, ABx chromatography, and the like, filtration, and so forth. The antibodies may be used in immunoassays to detect the presence or amount of a sirolimus compound such as, for example, rapamycin. In addition, the antibodies may be labeled or unlabeled or may be bound to a solid support.

An antibody selected for use in an immunoassay for rapamycin, for example, should specifically and preferentially bind rapamycin and its pharmaceutically active metabolites over other ligands such as other metabolites or related drugs such as FK 506 (Tacrolimus). In general, an antibody should be capable of distinguishing between one ligand relative to a second ligand. At least about 5-fold, at least about 10-fold, or at least about 20-fold, of the first ligand or ligands will be bound to the antibody if the antibody is combined with a sample containing the ligands. While the binding also depends on relative concentration of the ligands, the binding will be higher for the first ligand if the binding constant for the first ligand is greater than the binding constant for the second ligand, at least about 10-fold higher or at least about 50-fold higher and up to 1000-fold or higher. The phrase "at least about" means that the number of ligands bound is equal to or greater than the designated number and that the designated number may vary by plus or minus ten percent.

In one specific embodiment, a polyclonal antibody is raised against a compound above wherein the moiety is a poly(amino acid) immunogenic carrier or a-non-poly(amino acid) immunogenic carrier at position 32.

In another specific embodiment, a polyclonal or monoclonal antibody is raised against a compound above wherein the moiety is a poly(amino acid) immunogenic carrier or a non-poly(amino acid) immunogenic carrier at position 26.

The label conjugates and/or antibodies of the present invention may be employed in reagent systems for conducting various assay formats. Such assays usually involve reactions between binding partners such as a sirolimus compound analyte and a corresponding antibody or the binding between an antibody and a corresponding binding partner such as a second antibody that binds to the first antibody. Accordingly, the binding partner may be a protein, which may be an antibody or an antigen. The binding partner may be a member of a specific binding pair ("sbp member"), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as biotin-avidin, hormones-hormone receptors, enzyme-substrate, nucleic acid duplexes, IgG-protein A, polynucleotide pairs such as DNA-DNA, DNA-RNA, and the like are not immunological pairs but are included within the scope of sbp member.

Accordingly, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. Preferred binding partners are antibodies.

The aforementioned reagents may be employed in all types of immunoassays to determine the presence and/or amount of a sirolimus compound analyte in a sample suspected of containing such analytes. The immunoassays may involve labeled or non-labeled reagents. Immunoassays involving non-labeled reagents usually comprise the formation of relatively large antigen-antibody complexes. Such assays include, for example, immunoprecipitin and agglutination methods and corresponding light scattering techniques such as, e.g., nephelometry and turbidimetry, for the detection of antigen-antibody complexes. Labeled immunoassays include enzyme immunoassays, fluorescence polarization immunoassays, radioimmunoassay, inhibition assay, induced luminescence, fluorescent oxygen channeling assay, and so forth.

One general group of immunoassays includes immunoassays using the labeled conjugates of the invention with a limited concentration of antibody. Another group of immunoassays involves the use of an excess of all of the principal reagents. Such assays include two-site sandwich assays, e.g., immunoradiometric assays, immunofluorometric assays, immunochemi-luminometric assays, ELISA assays, and so forth. Another group of immnunoassays are separation-free homogeneous assays in which the labeled reagents modulate the label signal upon antigen-antibody binding reactions. Another group of assays includes labeled antibody reagent limited competitive assays for hapten or antigen that avoid the use of problematic labeled antigens or haptens. In this type of assay, the solid phase immobilized analyte be present in a constant, limited amount. The partition of a label between the immobilized analyte and free analyte depends on the concentration of analyte in the sample.

The assays can be performed either without separation (homogeneous) or with separation (heterogeneous) of any of the assay components or products. Homogeneous immunoassays are exemplified by the EMIT® assay (Syva Company, San Jose, Calif.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354, 693; and so forth.

Other enzyme immunoassays are the enzyme modulate mediated immunoassay ("EMMIA") discussed by Ngo and Lenhoff, FEBS Lett. (1980) 116.285–288; the substrate labeled fluorescence immunoassay ("SLFIA") disclosed by Oellerich, J. Clin. Chem. Clin. Biochem. (1984) 22:895–904; the combined enzyme donor immunoassays ("CEDIA") disclosed by Khanna, et al., Clin. Chem. Acta (1989) 185:231–240; homogeneous particle labeled immunoassays such as particle enhanced turbidimetric inhibition immunoassays ("PETINIA"), particle enhanced turbidimetric immunoassay ("PETIA"), etc.; and the like.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and so forth. Other types of assays include immunosensor assays involving the monitoring of the changes in the optical, acoustic and electrical properties of an antibody-immobilized surface upon the binding of an antigen or hapten. Such assays include, for example, optical immunosensor assays, acoustic immunosensor assays, semiconductor immunosensor assays, electrochemical transducer immunosensor assays, potentiometric immunosensor assays, amperometric electrode assays, and the like.

Exemplary of heterogeneous assays are the enzyme linked immunosorbant assay ("ELISA") mentioned briefly above and discussed in Maggio, E. T. supra; the radioimmunoassay, disclosed in Yalow, et al., *J. Clin. Invest.* 39:1157 (1960) and so forth.

The sirolimus compound conjugates and antibodies may be employed in an induced luminescence immunoassay, which is described in U.S. Pat. No. 5,340,716 (Ullman, et al.) entitled "Assay Method Utilizing Photoactivated Chemiluminescent Label" ("induced luminescence assay"), which disclosure is incorporated herein by reference. In one approach the assay uses a particle incorporating a photosensitizer and a label particle incorporating a chemiluminescent compound. The label particle is conjugated to an sbp member that is capable of binding to an analyte to form a complex, or to a second sbp member to form a complex, in relation to the presence of the analyte. If the analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which in turn is related to the amount of analyte present.

By way of further illustration, a chemiluminescent particle is employed, which comprises the chemiluminescent compound associated therewith such as by incorporation therein or attachment thereto. An sbp member that binds to the analyte, such as, for example, an antibody for a sirolimus compound produced from the aforementioned immunogenic carrier conjugates, is bound to a polysaccharide coating these particles. A second sbp member that binds to the analyte is part of a biotin conjugate. Streptavidin is conjugated to a second set of particles having a photosensitizer associated therewith. The binding of the streptavidin to this second set of particles (photosensitizer particles) may or may not involve a polysaccharide on the particles. The chemiluminescent particles are mixed with a sample suspected of containing a sirolimus compound analyte and the photosensitizer particles. The reaction medium is incubated to allow the particles to bind to the analyte by virtue of the binding of the sbp members to the analyte. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the analyte, it is activated by the singlet oxygen and emits luminescence. The medium is then examined for the presence and/or the amount of luminescence or light emitted, the presence thereof being related to the presence of the sirolimus compound analyte.

Another particular example of an assay to which the present conjugates and antibodies have application is discussed in U.S. Pat. No. 5,616,719 (Davalian, et al.), which describes fluorescent oxygen channeling immunoassays.

The above reagents may also be employed in multi-analyte immunoassays where the sirolimus compound analyte may be the subject of detection along with one or more other analytes such as other drugs and the like. Such multi-analyte systems are described, for example, in Loor, et al., J. Anal. Toxicol. 12: 299 (1988).

The homogeneous or heterogeneous assays discussed above are normally carried out in an aqueous buffered medium at a moderate pH, generally that which provides optimum assay sensitivity. The aqueous medium may be solely water or may include from 0.1 to about 40 volume percent of a cosolvent. The pH for the medium will usually be in the range of about 4 to about 11, more usually in the range of about 5 to about 10, and preferably in the range of about 6.5 to about 9.5. The pH will usually be a compromise between optimum binding of the binding members of any specific binding pairs, the pH optimum for other reagents of the assay such as members of the signal producing system, and so forth.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred. Various ancillary materials may be employed in the above methods. For example, in addition to buffers the medium may comprise stabilizers for the medium and for the reagents employed. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

One or more incubation periods may be applied to the medium at one or more intervals including any intervals between addition of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 50 to about 99° C., usually from about 15° C. to about 70° C., more usually 20° C. to about 45° C. The time period for the incubation is about 0.2 seconds to about 6 hours, usually, from about 2 seconds to about 1 hour, more usually, about 1 to about 5 minutes. The time period depends on the temperature of the medium and the rate of binding of the various reagents, which is determined by the association rate constant, the concentration, the binding constant and dissociation rate constant. Temperatures during measurements will generally range from about 10 to about 50° C., more usually from about 15 to about 40° C.

The concentration of analyte that may be assayed generally varies from about $10^{-5}$ to about $10^{-17}$ M, more usually from about $10^{-6}$ to about $10^{-14}$ M. Considerations, such as whether the assay is qualitative, semi-quantitative or quantitative (relative to the amount of analyte present in the sample), the particular detection technique and the concentration of the analyte normally determine the concentrations of the various reagents.

The concentrations of the various reagents in the assay medium will generally be determined by the concentration range of interest of the sirolimus compound analyte. However, the final concentration of each of the reagents is normally determined empirically to optimize the sensitivity of the assay over the range. That is, a variation in concentration of analyte that is of significance should provide an accurately measurable signal difference. Considerations such as the nature of the signal producing system and the nature of the analytes normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition as discussed above.

The following examples further describe the specific embodiments of the invention by way of illustration and not limitation and are intended to describe and not to limit the scope of the invention.

In a homogeneous assay after all of the reagents have been combined, the signal is determined and related to the amount of analyte in the sample. For example, in an EMIT assay for a sirolimus compound, a sample suspected of containing a sirolimus compound is combined in an aqueous medium either simultaneously or sequentially with an enzyme conjugate of a sirolimus compound of the invention and antibody capable of recognizing a sirolimus compound. Generally, a substrate for the enzyme is added, which results in the formation of a chromogenic or fluorogenic product upon enzyme catalyzed reaction. Preferred enzymes are glucose-6-phosphate dehydrogenase and alkaline phosphatase but other enzymes may be employed. The analytes and the moieties of the enzyme conjugate compete for binding sites on the antibody. The enzyme activity in the medium is then determined, usually by spectrophotometric means, and is compared to the enzyme activity determined when calibrators or reference samples are tested in which a known amount of the analytes is present. Typically, the calibrators are tested in a manner similar to the testing of the sample suspected of containing the analytes. The calibrators typically contain differing, but known, concentrations of the analyte to be determined. Preferably, the concentration ranges present in the calibrators span the range of suspected analyte concentrations in the unknown samples.

The aforementioned assays may be carried out using mutant glucose-6-phosphate dehydrogenase as the enzyme of the enzyme conjugate. This mutant enzyme is described in U.S. Pat. Nos. 6,090,567 and 6,033,890, the relevant disclosures of which are incorporated herein by reference. Furthermore, the assay may be conducted using antibodies for a sirolimus compound and using procedures as disclosed in U.S. Pat. Nos. 5,328,828 and 5,135,863, the relevant disclosures of which are incorporated herein by reference.

Heterogeneous assays usually involve one or more separation steps and can be competitive or non-competitive. A variety of competitive and non-competitive assay formats are disclosed in Davalian, et al., U.S. Pat. No. 5,089,390, column 14, line 25 to column 15, line 9, incorporated herein by reference. In one type of competitive assay using reagents in accordance with embodiments of the present invention, a support, as discussed above, having antibodies for a sirolimus compound bound thereto is contacted with a medium containing the sample and appropriate enzyme conjugates of the invention. After separating the support and the medium, the enzyme activity of the support or the medium is determined by conventional techniques and related to the presence and/or amount of a sirolimus compound in the sample.

Activation of a signal producing system depends on the nature of the signal producing system members. For those members of a signal producing system that are activated with light, the member is irradiated with light. For members of signal producing systems that are on the surface of a particle, addition of a base may result in activation. Other activation methods will be suggested to those skilled in the art in view of the disclosures herein. For some signal producing systems, no agent for activation is necessary such as those systems that involve a label that is a radioactive label, an enzyme, and so forth. For enzyme systems addition of a substrate and/or a cofactor may be necessary.

In certain embodiments a second enzyme may be employed in addition to the enzyme of the enzyme conjugate. The enzymes of the pair of enzymes are related in that a product of the first enzyme serves as a substrate for the second enzyme.

The examination for presence and amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, actinometer, photographic instrument, and the like. The presence and amount of signal detected is related to the presence and amount of the sirolimus compound present in a sample. Temperatures during measurements generally range from about 100 to about 70° C., more usually from about 20° to about 45° C., more usually about 20° to about 25° C. In one approach standard curves are formed using known concentrations of the analytes to be screened. As discussed above, calibrators and other controls may also be used.

The sample analyzed may be biological tissue, which includes excised tissue from an organ or other body part of a host and body fluids, for example, whole blood, plasma, serum, urine, saliva, semen, stool, sputum, cerebral spinal fluid, tears, mucus, and the like. In many instances, the sample is plasma or serum.

Another embodiment of an assay format is a capture assay. In this assay format, the antibody for rapamycin is covalently bound to a magnetic particle. The sample is incubated with these particles to allow the rapamycin in the sample to bind to the antibodies. Subsequently, an enzyme that has rapamycin or a rapamycin derivative covalently attached is incubated with the magnetic particles. After washing, the amount of enzyme that is bound to the magnetic particles is measured and is inversely related to the presence and/or amount of rapamycin in the sample.

The following specific assay descriptions are by way of illustration and not limitation on the scope of the present invention. Selection of rapamycin as the sirolimus compound is also by way of illustration and not limitation as the present invention has general application to detection of sirolimus compounds.

In one embodiment, rapamycin-label compounds of embodiments of this invention can be used in an immunoassay or receptor based assay as the first part of the detection molecule by mixing the test sample or a rapamycin standard with a rapamycin-oxime conjugate such as a biotin ester of rapamycin and allowing them to compete for binding to the antibody or a receptor such as an FK binding protein. After rinsing with an appropriate wash buffer, a detection molecule consisting of streptavidin or avidin conjugated to an enzyme, florescent or chemiluminescent molecule or radioactive moiety can be used.

In one embodiment the assay is an induced luminescence assay as described above. The reagents include two latex bead reagents and a biotinylated anti-rapamycin mouse monoclonal antibody. This antibody may be an antibody raised against a position 26 or position 32 rapamycin immunogen as described above or it may be an antibody raised against a known rapamycin immunogen. The first bead reagent is coated with rapamycin or a rapamycin analog and contains chemiluminescent dye. The rapamycin coated on the first bead reagent may be attached to the surface of the first bead reagent by linking through position 26 or position 32 in accordance with the embodiments discussed above or it may be attached at other positions as known in the art. At least one of the antibody for rapamycin or the rapamycin on the first bead reagent is in accordance with embodiments of the invention discussed above. The second bead reagent is coated with streptavidin and contains a photosensitizer dye. In a first step, sample is incubated with biotinylated antibody, which allows rapamycin from the sample to saturate a fraction of the biotinylated antibody that is directly related to the rapamycin concentration. In a second step, the first bead reagent is added and leads to the formation of bead/biotinylated antibody immunocomplexes with the non-saturated fraction of the biotinylated antibody. The second bead reagent is then added and binds to the biotin to form bead pair immunocomplexes. When illuminated by light at 680 nm, the second bead reagent converts dissolved oxygen in the reaction solution into the more energetic singlet oxygen form (1O2). In the bead pairs, the singlet oxygen diffuses into the first bead reagent thereby triggering a chemiluminescent reaction. The resulting chemiluminescent signal is measured at 612 nm and is an inverse function of the concentration of rapamycin in the sample. The amount of this signal is related to the presence of amount of rapamycin in the sample.

A specific example of another assay format is ACMIA (Affinity Column Mediated Immuno Assay). For the ACMIA assay format, chrome particles, which are coated with rapamycin or a rapamycin analog, are employed as a first component. A second component is an antibody for rapamycin. This antibody is crosslinked to a reporter enzyme (usually beta-galactosidase) and is added to a reaction vessel in excess. The antibody-enzyme conjugate is mixed with a sample to allow the analyte to bind to the antibody. Next, the chrome reagent is added to bind up any excess antibody-enzyme conjugate. Then, a magnet is applied, which pulls all of the chrome and excess antibody-enzyme out of the suspension, and the supernatant is transferred to a final reaction container. The substrate of the reporter enzyme is added to the final reaction container, and the enzyme activity is measured spectrophotometrically as a change in absorbance over time. At least one of the antibody for rapamycin as part of the second component or the rapamycin on the chrome particles is in accordance with embodiments of the invention discussed above. The amount of this signal is related to the presence of amount of rapamycin in the sample.

In a sandwich assay format, a first reagent comprising chrome particles coated with anti-rapamycin antibodies (or rapamycin binding protein), and a second reagent comprising a second antibody (or binding protein) conjugated to a reporter enzyme are employed. In this format, the sample is incubated with the chrome particles so that all of the rapamycin in the sample becomes bound to the chrome particles. The chrome particles are washed, using a magnet to separate the bound analyte from the supernatant. Then, the second reagent, i.e., antibody (or binding protein) conjugated to a reporter enzyme, is incubated with the chrome particles to form a "sandwich". After washing, the amount of enzyme that is bound to the chrome is measured and is related to the presence and/or amount of rapamycin in the sample. At least one of the antibodies of the first and second antibody reagents is in accordance with embodiments of the invention discussed above.

Another assay format is EMIT (Enzyme-Mediated Immunoassay Technology). In this assay format, an enzyme conjugate is formed such as, for example, a conjugate of G-6-PDH and rapamycin. An antibody for rapamycin is incubated with the enzyme-conjugate and a sample suspected of containing rapamycin. Antibody for rapamycin binds to the rapamycin analyte in the sample instead of binding to the enzyme conjugate, which reduces the amount of inhibition of the enzyme activity that might otherwise occur in the absence of rapamycin in the sample. In this way, samples with more analyte will yield higher enzyme activity, and samples with no analyte will have the maximum inhibition and the lowest enzyme activity. The amount of reduction of inhibition of enzyme activity is related to the amount of rapamycin in the sample. At least one of the antibody for rapamycin or the rapamycin of the rapamycin-enzyme conjugate is in accordance with embodiments of the invention discussed above.

Another aspect of the present invention relates to kits useful for conveniently performing an assay for the determination of a sirolimus compound. In one embodiment a kit comprises in packaged combination an antibody for a sirolimus compound and an enzyme conjugate in accordance with embodiments of the invention. In another embodiment a kit of the invention comprises in packaged combination a conjugate of an enzyme and a sirolimus compound, an antibody for a sirolimus compound raised against a conjugate of a sirolimus compound and an immunogenic carrier in accordance with embodiments of the invention. Other kit embodiments are also included and the reagents in the kit depend upon the particular assay format. However, at least one of the reagents comprises an antibody raised against an immunogen in accordance with embodiments of the present invention or comprises a label conjugate in accordance with embodiments of the present invention or both.

To enhance the versatility of the subject invention, the kit reagents can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents.

The kit can further include other separately packaged reagents for conducting an assay such as additional sbp members, ancillary reagents such as an ancillary enzyme substrate, and so forth. The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

Specific Embodiments

Examples of specific embodiments of the invention include the following.

A compound comprising a moiety, selected from the group consisting of poly(amino acid) label moieties, non-poly(amino acid) label moieties, poly(amino acid) immunogenic carriers, non-poly(amino acid) immunogenic carriers, non-label poly(amino acid) moieties, and non-immunogenic carrier poly(amino acid) moieties linked to a sirolimus compound at position 26.

A compound according to the above wherein the moiety is linked to the sirolimus compound at position 26 by a linking group.

A compound according to the above wherein the linking group comprises an oxime functionality.

A compound according to the above wherein the moiety is a non-poly(amino acid) immunogenic carrier selected from the group consisting of polysaccharides, nucleic acids and particles or a poly(amino acid) immunogenic carrier selected from the group consisting of albumins and globulins.

A compound according to the above wherein the moiety is a poly(amino acid) label that is an enzyme or a non-poly(amino acid) label moiety selected from the group consisting of polynucleotides coding for a catalyst, promoters, dyes, fluorescent molecules, chemiluminescent molecules, coenzymes, enzyme substrates, radioactive groups, small organic molecules, amplifiable polynucleotide sequences, and particles.

A compound according to the above of the structure:

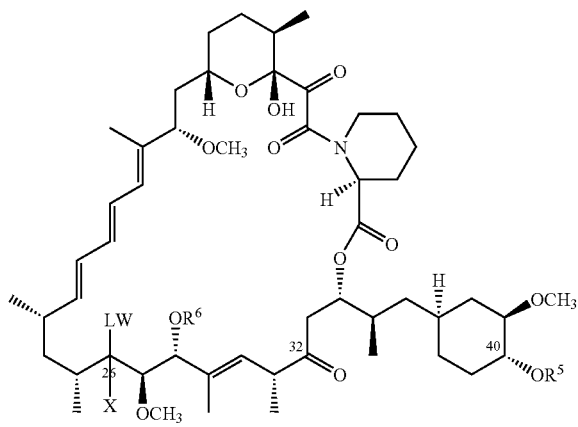

wherein L is a linking group, X is hydrogen, $R^5$ and $R^6$ are independently selected from hydrogen, $C_{1-7}$ alkyl, or $C(O)$ $C_{1-6}$ alkyl, and W is a moiety, selected from the group consisting of poly(amino acids), non-poly(amino acid) label moieties, and non-poly(amino acid) immunogenic carriers.

An antibody raised against a compound according to the above wherein the moiety is a poly(amino acid) immunogenic carrier or a non-poly(amino acid) immunogenic carrier linked at position 26.

A compound according to the above wherein the sirolimus compound is rapamycin or a derivative thereof.

A polyclonal antibody raised against a compound comprising a moiety, selected from the group consisting of poly(amino acid) immunogenic carriers and non-poly(amino acid) immunogenic carriers, linked to a sirolimus compound at position 32.

A compound of structure I:

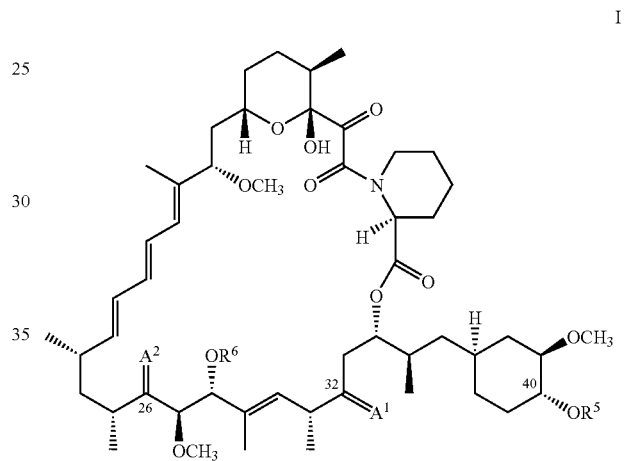

wherein $A^1$ and $A^2$ are independently oxo or a group of the formula:

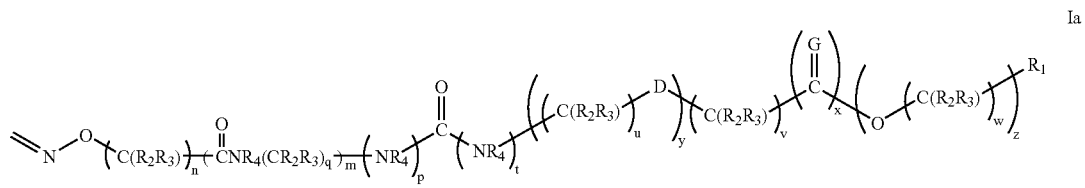

with the proviso that both $A^1$ and $A^2$ cannot be oxo and wherein:
n, q, u, v and w are independently 0 to about 12,
m is 0 or 1,
p is 0 or 1,
t is 0 or 1,
y is 0 to about 5,
x is 0 or 1,
z is 0 or 1, D is O or S, G is O or NR$^2$, with the proviso that, when A$^1$ is not oxo, then at least one of m is 1, or t is 1, or y is 1 to about 5, or v is 1 to about 12, or x is 1, or z is 1, or, when A$^1$ is not oxo, then R$^1$ is II, R$^1$ is a moiety, selected from the group consisting of functional groups, poly(amino acid) label moieties, poly(amino acid) immunogenic carriers, non-poly(amino acid) label moieties, and non-poly(amino acid) immunogenic carriers, or

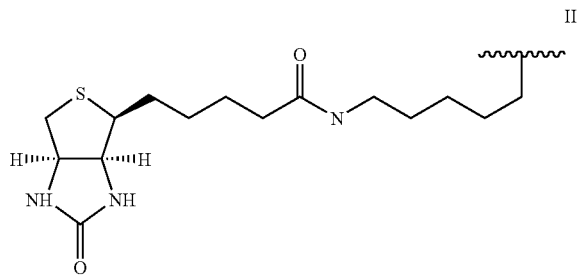

II

R$^2$ and R$^3$ are independently selected from hydrogen, C$_{1-10}$ alkyl, benzyl, OH, halogen, C$_{1-6}$ alkoxy; C$_{3-10}$ alkenyl, and C$_{3-10}$ alkynyl, R$^4$ is independently hydrogen, C$_{1-10}$ alkyl, benzyl, C$_{3-10}$ alkenyl, C$_{3-10}$ alkynyl; and R$^5$ and R$^6$ are independently selected from hydrogen; phenyl; substituted phenyl in which the substituents are X, Y and Z; 1- or 2-naphthyl; substituted 1- or 2-naphthyl in which the substituents are X, Y and Z; C(O)C$_{1-6}$ alkyl; C$_{1-10}$ alkyl; C$_3$–C$_{10}$ cycloalkyl; substituted C$_{1-10}$ alkyl in which one or more substituent(s) is(are) selected from hydroxy, oxo, C$_{1-6}$-alkoxy; phenyl, substituted phenyl in which the substituents on phenyl are X, Y and Z and OC(O)C$_{1-6}$ alkyl; C$_{3-10}$ alkenyl; C$_{4-10}$ cycloalkenyl; substituted C$_{3-10}$ alkenyl in which one or more substituent(s) is(are) selected from hydroxy, oxo, C$_{1-6}$-alkoxy, phenyl, substituted phenyl in which the substituents on phenyl are X, Y and Z and OC(O)C$_{1-6}$ alkyl; C$_{3-10}$ alkynyl; and substituted C$_{3-10}$ alkynyl in which one or more substituent(s) is(are) selected from hydroxy, oxo, C$_{1-6}$-alkoxy, phenyl, substituted phenyl, in which the substituents on phenyl are X, Y and Z and OC(O)C$_{1-6}$ alkyl;

X, Y and Z are independently selected from: hydrogen; C$_{1-7}$ alkyl; C$_{2-6}$ alkenyl; halogen; CN; C(O)H; perhalosubstituted groups; SR$^7$, wherein R$^7$ is hydrogen, C$_{1-6}$ alkyl, CF$_3$ or phenyl; SOR$^7$, wherein R$^7$ is as defined above; SO$_2$R$^7$, wherein R$^7$ is as defined above; CONR$^5$R$^6$, wherein R$^5$ and R$^6$ are as defined above; —(CH$_2$)$_r$OR$^8$, wherein R$^8$ is hydrogen, C$_{1-3}$ alkyl; hydroxy-C$_{2-3}$ alkyl, and r is 0–2; C$_{1-3}$ alkyl; hydroxy-C$_{2-3}$ alkyl; CH(OR$^9$)(OR$^{10}$), wherein R$^9$ and R$^{10}$ are C$_{1-3}$ alkyl or taken together form an ethyl or propyl bridge; —CH$_2$)$_r$OC(O)R$^8$, wherein R$^8$ and r are as defined above, and —(CH$_2$)$_r$C(O)OR$^8$, wherein R$^8$ and r are as defined above.

A compound according to the above wherein m is 0 and p is 1.

A compound according to the above wherein m is 1 and p is 1.

A compound according to the above wherein m and p are each 0.

A compound according to the above wherein the moiety is an immunogenic carrier selected from the group consisting of poly(amino acids), polysaccharides, nucleic acids and particles.

A compound according to the above wherein the moiety is a label selected from the group consisting of enzymes, polynucleotides coding for a catalyst, promoters, dyes, fluorescent molecules, chemiluminescent molecules, coenzymes, enzyme substrates, radioactive groups, small organic molecules, amplifiable polynucleotide sequences, and particles.

A compound according to the above wherein R$^2$ and R$^3$ and R$^4$ are hydrogen, R$^5$ and R$^6$ are independently hydrogen, C$_{1-7}$ alkyl or C(O)C$_{1-6}$ alkyl and A$^2$ is oxo.

A compound according to the above wherein R$^2$ and R$^3$and R$^4$ are hydrogen, R$^5$ and R$^6$ are independently hydrogen, C$_{1-7}$ alkyl, or C(O)C$_{1-6}$ alkyl and A$^2$ is oxo.

A compound according to the above wherein R$^2$ and R$^3$ and R$^4$ are hydrogen, R$^5$ and R$^6$ are independently hydrogen, C$_{1-7}$ alkyl, or C(O)C$_{1-6}$ alkyl and A$^2$ is oxo.

A compound according to the above wherein R$^2$ and R and R$^4$ are hydrogen, R$^5$ and R$^6$ are independently hydrogen, C$_{1-7}$ alkyl, or C(O)C$_{1-6}$ alkyl and A$^1$ is oxo.

A compound according to the above wherein R$^2$ and R$^3$ and R$^4$ are hydrogen, R$^5$ and R$^6$ are independently hydrogen, C$_{1-7}$ alkyl, or C(O)C$_{1-6}$ alkyl and A$^1$ is oxo.

A compound according to the above wherein R$^2$ and R$^3$ and R$^4$ are hydrogen, R$^5$ and R$^6$ are independently hydrogen, C$_{1-7}$ alkyl, or C(O)C$_{1-6}$ alkyl and A$^1$ is oxo.

A compound according to the above wherein the moiety is a poly(amino acid) immunogenic carrier selected from the group consisting of bovine serum albumin, keyhole limpet hemocyanin, egg ovalbumin, and bovine gamma-globulin.

A compound according to the above wherein the moiety is a poly(amino acid) label moiety that is an enzyme.

A compound according to the above wherein group Ia has the formula:

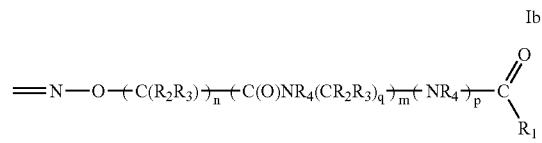

Ib with the proviso that, when A$^1$ is not oxo, then m is 1, or, when A$^1$ is not oxo, then R$^1$ is II, A compound according to the above wherein group Ia has the formula:

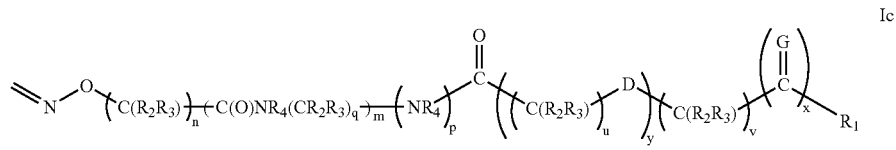

Ic with the proviso that, when $A^1$ is not oxo, then at least one of m is 1, or t is 1, or y is 1 to about 5, or v is 1 to about 12, or x is 1, or, when $A^1$ is not oxo, then $R^1$ is II, A compound according to the above wherein group Ia has the formula:

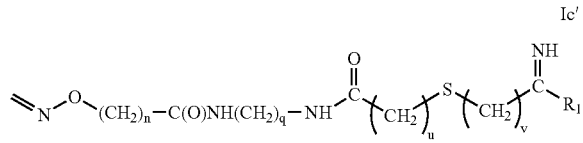

including imine salts thereof.

A compound according to the above wherein group Ia has the formula:

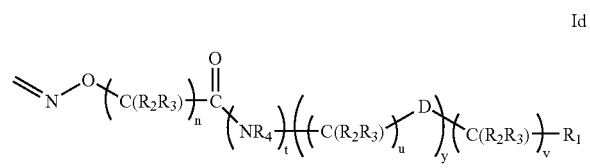

with the proviso that, when $A^1$ is not oxo, then at least one of t is 1, or y is 1 to about 5, or v is 1 to about 12, or, when $A^1$ is not oxo, then $R^1$ is II, A compound according to the above wherein group Ia has the formula:

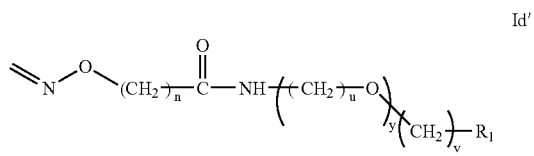

wherein n is 1, u is 2, y is 2 and v is 1 and wherein $R^1$ is linked through an amine moiety of $R^1$ A polyclonal antibody raised against a compound according to the above wherein the moiety is a poly(amino acid) immunogenic carrier or a non-poly(amino acid) immunogenic carrier at position 32.

An antibody raised against a compound according to the above wherein the moiety is a poly(amino acid) immunogenic carrier or a non-poly(amino acid) immunogenic carrier at position 26.

A kit comprising an antibody according to the above and a conjugate of a sirolimus compound and a label.

A kit comprising an antibody according to the above and a conjugate of a sirolimus compound and a label.

A kit comprising an antibody for a sirolimus compound and a compound according to the above wherein the moiety is a poly(amino acid) label or a non-poly(amino acid) label.

A kit according to the above wherein the moiety is a non-poly(amino acid) label that is a chrome particle.

A kit according to the above wherein the moiety is a poly(amino acid) label that is an enzyme.

A kit according to the above wherein the enzyme is glucose-6-phosphate dehydrogenase.

A method for determining a sirolimus compound in a sample suspected of containing a sirolimus compound, the method comprising:
(a) providing in combination in a medium:
(i) the sample,
(ii) an antibody for the sirolimus compound, and
(iii) a compound according to the above wherein the moiety is a poly(amino acid) label or a non-poly(amino acid) label, and
(b) examining the medium for the presence of a complex comprising the sirolimus compound and the antibody for sirolimus, the presence thereof indicating the presence of the sirolimus compound in the sample.

A method for determining a sirolimus compound in a sample suspected of containing a sirolimus compound, the method comprising:
(a) providing in combination in a medium:
(i) the sample,
(ii) an antibody according to the above, and
(iii) a label conjugate of sirolimus compound, and
(b) examining the medium for the presence of a complex comprising the sirolimus compound and the antibody for sirolimus, the presence thereof indicating the presence of the sirolimus compound in the sample, A method for determining a sirolimus compound in a sample suspected of containing a sirolimus compound, the method comprising:
(a) providing in combination in a medium:
(i) the sample,
(ii) an antibody according to the above, and
(iii) a label conjugate of sirolimus compound, and
(b) examining the medium for the presence of a complex comprising the sirolimus compound and the antibody for sirolimus, the presence thereof indicating the presence of the sirolimus compound in the sample.

A sirolimus compound according to the above wherein the sirolimus compound of structure I is linked to a polysaccharide by means of Ia and wherein the polysaccharide is further linked to a particle.

A sirolimus compound according to the above wherein the particle is a chrome particle.

A homogeneous method for determining the presence or amount of a sirolimus compound in a medium suspected of containing a sirolimus compound, the method comprising:
a) providing in combination (1) a medium suspected of containing the sirolimus compound, (2) a photosensitizer associated with a first particle and being capable of generating singlet oxygen, and (3) a chemiluminescent composition activatable by singlet oxygen and associated with a second particle, wherein an antibody according to the above is associated with the first particle or the second particle or both,
b) subjecting the combination to conditions for binding of the antibody to the sirolimus compound, if present, and
c) irradiating the photosensitizer with light and detecting the amount of luminescence generated by the chemiluminescent composition, the amount thereof being related to the amount of each of the components in the medium.

A method according to the above wherein the antibody is associated with the first particle by virtue of being bound to a small molecule and the particle comprises a binding partner for the small molecule.

A method according to the above wherein the small molecule is biotin and the binding partner is streptavidin.

A method according to the above wherein second particle is coated with a rapamycin analog.

A homogeneous method for determining the presence or amount of a sirolimus compound in a medium suspected of containing a sirolimus compound, the method comprising:

a) providing in combination (1) a medium suspected of containing the sirolimus compound, (2) a photosensitizer associated with a first particle and being capable of generating singlet oxygen, and (3) a chemiluminescent composition activatable by singlet oxygen and associated with a second particle, wherein an antibody according to the above is associated with the first particle or the second particle or both, b) subjecting the combination to conditions for binding of the antibody to the sirolimus compound, if present, and c) irradiating the photosensitizer with light and detecting the amount of luminescence generated by the chemiluminescent composition, the amount thereof being related to the amount of each of the components in the medium.

A method according to the above wherein the antibody is associated with the first particle by virtue of being bound to a small molecule and the particle comprises a binding partner for the small molecule.

A method according to the above wherein the small molecule is biotin and the binding partner is streptavidin.

A method according to the above wherein second particle is coated with a rapamycin analog.

A homogeneous method for determining the presence or amount of a sirolimus compound in a medium suspected of containing a sirolimus compound, the method comprising:

a) providing in combination (1) a medium suspected of containing the sirolimus compound, (2) a photosensitizer associated with a first particle and being capable of generating singlet oxygen, and (3) a chemiluminescent composition activatable by singlet oxygen and associated with a second particle, wherein an antibody for the sirolimus compound is associated with the first particle or the second particle or both and wherein the other of the first particle or the second particle is coated with a sirolimus compound of the above, b) subjecting the combination to conditions for binding of the antibody to the sirolimus compound, if present, and c) irradiating the photosensitizer with light and detecting the amount of luminescence generated by the chemiluminescent composition, the amount thereof being related to the amount of each of the components in the medium.

A method according to the above wherein the antibody is associated with the first particle by virtue of being bound to a small molecule and the particle comprises a binding partner for the small molecule.

A method according to the above wherein the small molecule is biotin and the binding partner is streptavidin.

A method according to the above wherein the second particle is coated with a sirolimus compound.

A sirolimus compound comprising a particle bound to the sirolimus compound by means of a linking group of the formula:

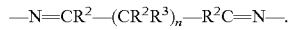

wherein $R^2$ and $R^3$ are independently selected from hydrogen, $C_{1-10}$ alkyl, benzyl, OH, halogen, $C_{1-6}$ alkoxy; $C_{3-10}$ alkenyl, and $C_{3-10}$ alkynyl.

A sirolimus compound according to the above having the general formula:

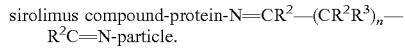

A sirolimus compound according to the above wherein the particle is a chrome particle.

The following examples further describe the specific embodiments of the invention by way of illustration and not limitation and are intended to describe and not to limit the scope of the invention.

EXAMPLES

Analytical thin layer chromatography (TLC, silica) is the usual analysis method and was performed using plates from Analtech, Newark Del. (Catalog No: VWRDU, scored 10×20 cm, 250 μm). Preparative thin layer chromatography (PTLC) separations were carried out on pre-coated silica gel plates from Whatman, Clifton N.J. (Catalog No: 4856-840, silica gel, 150 A°, 1000 μm) and Analtech (Catalog No: 02015, silica gel, 2000 μm). The reagents and solvents were commercial grades and used without further purification. Rapamycin was obtained from BioAge Pharmaceuticals Inc., San Diego, Calif. KLH, BSA and BCA protein assay reagents were obtained from Pierce Chemical Company, St. Louis Mo. $^1$H-NMR spectra were routinely recorded on a Bruker Ultrashiel™-400 (400 MHZ) spectrometer (Bruker Instruments, Bellerica, Mass. 01821). Chemical shifts were reported parts per million (ppm, δ); tetramethylsilane (TMS) or other deuterated solvents were used as the internal references. Mass spectra were obtained from the Mass spectrometry Laboratory, University of California at Berkeley, Calif.

Preparation of Compounds (2) and (3) (See FIG. 1)

To a solution of rapamycin (1) (1 g, 1.0545 mmol) and carboxymethyoxylamine hemihydrochloride (823 mg, 3.16 mmol) in methanol (MeOH) (41 mL), was added sodium acetate (263.0 mg, 3.18 mmol). The reaction mixture was stirred at room temperature under nitrogen atmosphere overnight and the progress of the reaction was monitored by TLC (silica gel) (MeOH/CH$_2$Cl$_2$=1/9). De-ionized water (40 mL) and methylene chloride (40 mL) were added into the mixture. Aqueous layer was extracted with methylene chloride (3×40 mL), combined organic layer was then washed with de-ionized water (20 mL), dried over Na$_2$SO$_4$, filtered and concentrated. This gave crude product (1.0774 g). Purification of the crude product (148.8 mg) with three preparative TLC plates (silica gel, 150 A°, 1000 μm, Whatman) (ethyl acetate (EtOAc)/Hexane/MeOH)=5/2/1 with an addition of glacial acetic acid) was performed to give two compounds (2) (32.6 mg, 45% yield) and (3) (39.4 mg, 55%). (2): mass spectrum (FAB; m/e: MNa$^+$, 1171.6); (3): mass spectrum (FAB; m/e: MNa$^+$, 1171.6).

Figure 2:
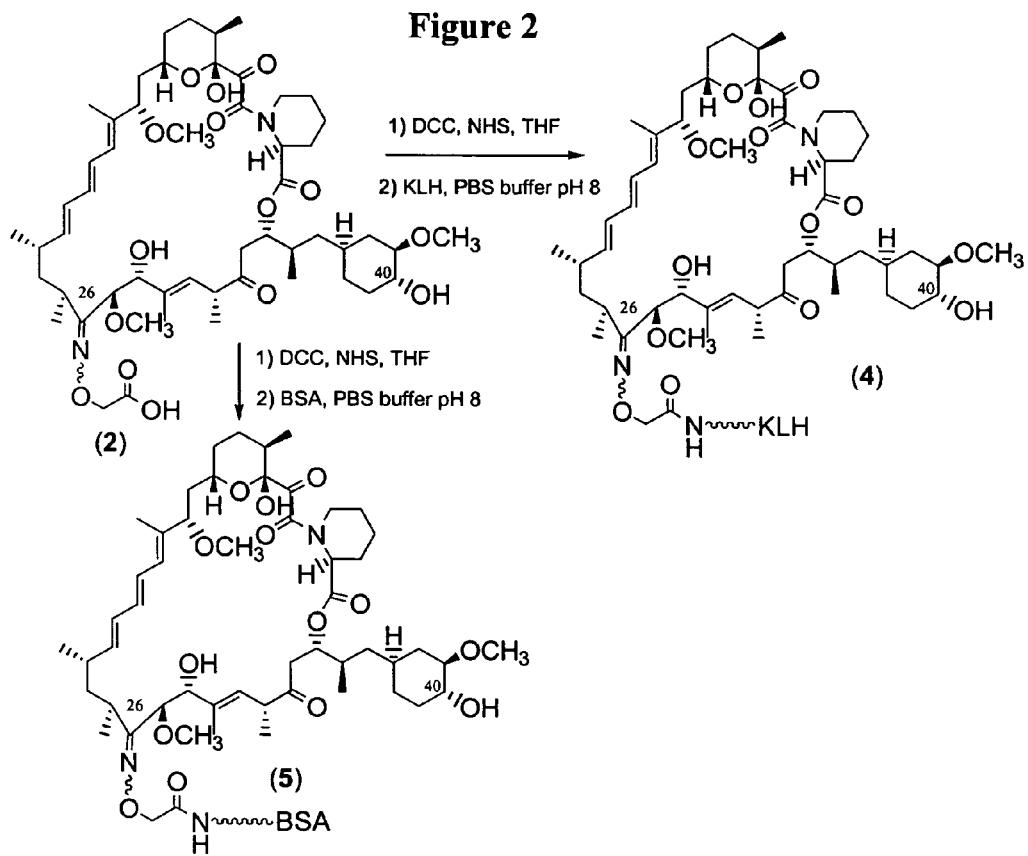
FIG. 2 is a scheme depicting the synthesis of protein derivatives of sirolimus compounds at position 26 where the proteins are KLH and BSA, respectively.

Preparation of KLH Immunogen (4) (See FIG. 2)

To a solution of (2) (70.1 mg, 0.071 mmol) in THF/DMF (6 mL THF, 0.1 mL DMF) were added N-hydroxysuccinimide (NHS) (12.8 mg, 0.108 mmol) and N,N-dicyclohexyl carbodiimide (DCC) (22.2 mg, 0.106 mmol). The reaction mixture was stirred at room temperature under nitrogen atmosphere and the product rapamycin (Rapa)-NHS ester is a spot less polar than compound (2). The reaction did not finish in six hours, so another batch of N-hydroxysuccinimide (NHS) (16.85 mg, 0;142 mmol) and N,N-Dicyclohexyl carbodiimide (DCC) (29.59 mg, 0.142 mmol) were added into the reaction mixture and the reaction finished in 16 hours. White solid formed during the reaction was filtered and then washed with EtOAC. After solvent was removed, the reaction mixture was re-dissolved in EtOAC and filtered; evaporation of solvent afforded a slight yellow liquid, which was kept under high vacuum for one hour.

The activated hapten Rapa-NHS ester was dissolved in dimethyl formamide (DMF) (2 mL) and added drop wise to a KLH (100 mg, 0.0362 mmol of $NH_2$) in PBS buffer (0.1 M $NaH_2PO_4/Na_2HPO_4$, pH 8) (30 mL) in an ice bath. After stirring for one hour at room temperature, pH of the solution was adjusted to 8 with NaOH (2N) and the mixture was stirred in a cold room (4° C.) overnight.

Rapamycin KLH immunogen was purified using an equilibrated SEPHADEX® G-25 column (C26×100) with PBS buffer (0.1 M $NaH_2PO_4/Na_2PO_4$, pH 7), eluted with the same PBS buffer. The UV detector at 280 nm monitored the eluted fractions from the column. A clean separation between KLH immunogen and the hapten was obtained. Fractions contained KLH immunogen (4) were pooled to a total of 75 mL, which was then concentrated through an Amica concentrator to 51 mL (Amica, model 8050, 50 ml from Millipore Corporation, Burlington Mass.). The concentration of the immunogen was determined by BCA Protein Concentration Assay and the hapten number by 2,4,6-trinitrobenzene sulfonic acid (TNBS) assay. The immunogen had a concentration of 1.60 mg/mL with a hapten number of 1072 and was used for the immunization of sheep to raise antibody.

Preparation of BSA Immunogen (5) (See FIG. 2)

To a solution of (2) (167.97 mg, 0.17 mmol) in tetrahydrofuran (THF)/DMF (8 mL THF, 0.4 mL DMF) were added N-hydroxysuccinimide (NHS) (41.8 mg, 0.35 mmol), N,N-dicyclohexyl carbodiimide (DCC) (70.9 mg, 0.34 mmol). The reaction mixture was stirred at room temperature under nitrogen atmosphere and the product Rapa-NHS ester is a spot less polar than compound (2). Two more batches of NHS and DCC, one batch with NHS (30.3 mg, 0.26 mmol) and DCC (53.1 mg, 0.25 mmol, another batch with NHS (20.2 mg, 0.17 mmol) and DCC (35.4 mg, 0.17 mmol) were added after 4 hours and 20 hours of reaction, respectively. The reaction finished in 24 hours. White solid formed during the reaction was filtered and then washed with EtOAc. After solvent was removed, the reaction mixture was re-dissolved in EtOAc and filtered; evaporation of solvent afforded a slight yellow liquid, which was under high vacuum for one hour.

The activated hapten Rapa-NHS ester was dissolved in DMF (1 mL) and added dropwise to a BSA (120 mg, 0.0896 mmol of NH2) in phosphate buffered saline (PBS) buffer (0.1 M $NaH_2PO_4/Na_2HPO_4$, pH 8) (14 mL) in an ice bath. After stirring for one hour at room temperature, pH of the solution was adjusted to 8 with NaOH (1N) and the mixture was stirred in a cold room (4° C.) overnight.

Rapamycin BSA immunogen was purified through an equilibrated SEPHADEX G-25 column (C26×70) with PBS buffer (0.1 M $NaH_2PO_4/Na_2PO_4$, pH 7), eluted with same PBS buffer. The UV detector at 280 nm monitored the eluted fractions from the column. A clean separation between BSA immunogen and the hapten was obtained. Fractions contained BSA immunogen (5) were pooled to a total of 57 mL, the concentration of the immunogen was determined by BCA Protein Concentration Assay and the hapten number by TNBS assay. The immunogen had a concentration of 2.52 mg/mL with a hapten number of 43 and was used for the immunization of sheep to raise antibody.

Figure 3:
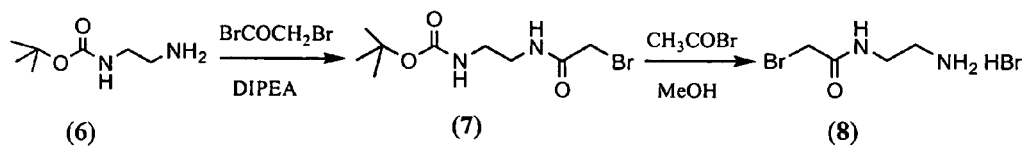
FIG. 3 is a scheme depicting the synthesis of a linking group used in the scheme depicted in FIG. 4 to link to the oxime functionality.

Preparation of Compound (7) (See FIG. 3)

To a 250 mL dried round bottom flask were added N-Boc-ethylenediamine (6) (1.0 g, 6.116 mmol), $CH_2Cl_2$ (100 mL) and N,N'-Diisopropylethylamine (DIPEA) (2.13 mL, 12.233 mmol). The mixture was stirred at 0° C. under nitrogen atmosphere for 10 minutes. Bromoacetyl bromide was then added through a syringe in 10 minutes in an ice bath. The progress of the reaction was monitored by TLC (silica gel, $MeOH/CH_2Cl_2=1/9$) and a less polar compound than bromoacetyl bromide was the product. The reaction finished in one hour. The mixture was washed with de-ionized water (2×20 mL). Aqueous layers were extracted with $CH_2Cl_2$ (2×20 mL). Combined organic phase was dried over $Na_2SO_4$, filtered and concentrated. Crude product was purified by flash column chromatography (silica gel) using $CH_2Cl_2/MeOH=97/3$ as an eluent to give desired product compound (7) (1.2290 g, 71% yield) as a yellow solid. $^1$H-NMR ($CDCl_3$, 400 MHZ) δ: 7.62 (bs, 1H), 5.59 (t, J=5.68 Hz, 1H), 3.88 (s, 2H), 3.41 (q, J=5.64 Hz, 2H), 3.31 (t, J=5.44 Hz, 2H), 1.44

Preparation of Compound (8) (See FIG. 3)

To a stirred solution of compound (7) (1.229 g, 4.37 mmol) in EtOAc (60 mL)/MeOH (0.45 mL) in an ice-water bath was added acetyl bromide (484.8 μL, 6.557 mmol), in one minute through a syringe. The mixture was stirred at 0° C. and the progress of the reaction was monitored by TLC (silica gel, $MeOH/CH_2Cl_2=5/95$). Solid started to form 5 minutes after adding the acetyl bromide. TLC indicated that the reaction did not finish after 5 hours. Another batch of acetyl bromide (323 μL, 4.37 mmol) was added to the mixture and the reaction finished in 6 hours. Solvent was decanted and 10 mL of EtOAc was added to the flask. After mixing and settling of solids, solvent was decanted again. The process was repeated until the pH of the solvent was about 5. A small amount solvent was removed by rotary evaporation, and the remainder was dried by high vacuum pump overnight. The product (8) was a light brownish solid (1.208 g, 105.6% yield). $^1$H-NMR ($CDCl_3$, 400 MHZ) δ: 3.92 (s, 2H), 3.51 (t, J=6.06 Hz, 2H), 3.10 (t, J=5.94

Figure 4:
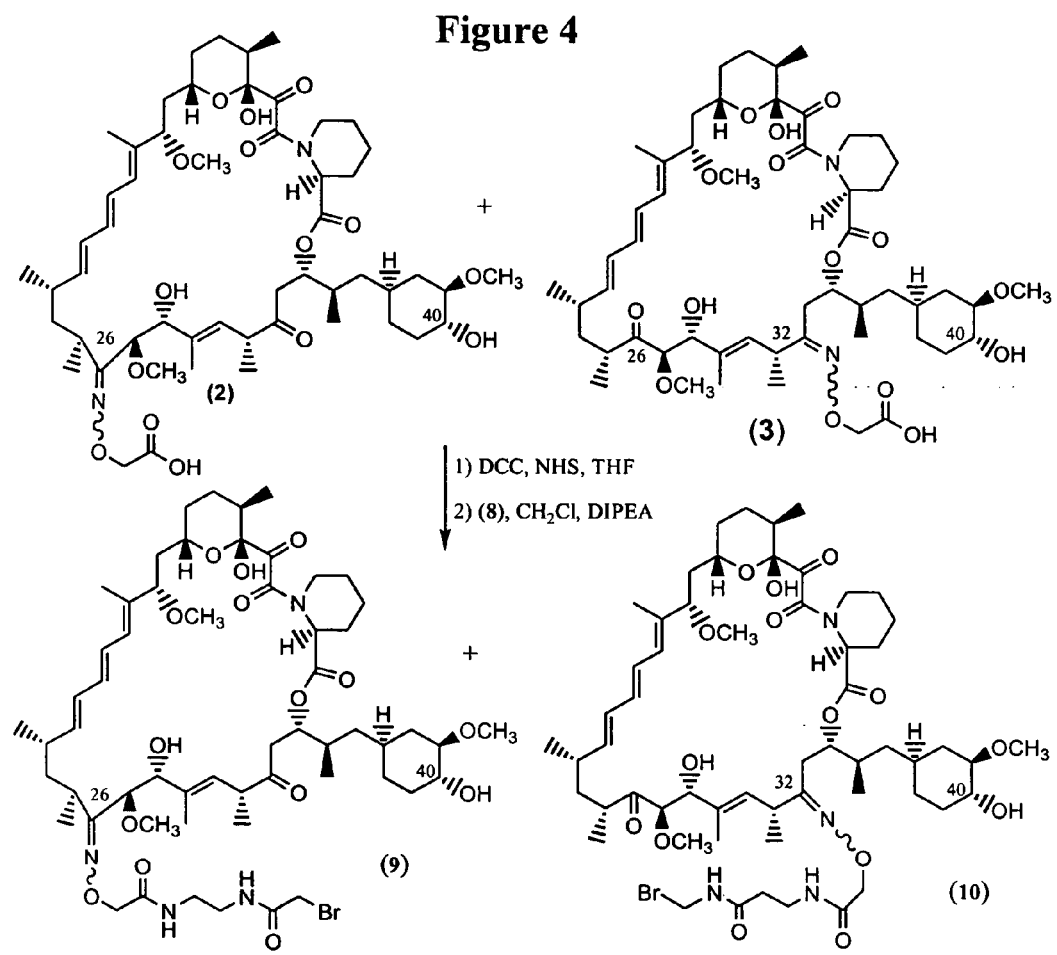
FIG. 4 is a scheme depicting the synthesis of oxime derivatives of sirolimus compounds at positions 26 and 32, respectively, using the linking group of FIG. 3.

Preparation of Compounds (9) and (10) (See FIG. 4)

To a solution of rapamycin oxime region-isomer mixture (2) and (3) (100.8 mg, 0.102 mmol) in THF (3.5 mL) were added NHS (36.4 mg, 0.307 mmol) and DCC (63.9 mg, 0.307 mmol). The mixture was stirred at room temperature under nitrogen atmosphere for six hours. The progress of the reaction was monitored by TLC (silica gel, $CH_2Cl_2/MeOH=1/19$) and product is a less polar compound than starting region-isomer. Solid that formed during the reaction was filtered and washed with ethyl acetate. After removal of solvent, compound was dissolved in ethyl acetate and was filtered; concentration of product afforded a white solid (177.4 mg). To this Rapa-NHS ester solution in $CH_2Cl_2$ (3 mL), were added compound (8) in $CH_2Cl_2$ and EtOAc (1 mL). After stirring for 10 minutes, DIPEA was added and reaction was stirred at room temperature under nitrogen atmosphere for 2 hours. De-ionized water (15 mL) was added to the flask and the pH of the solution was adjusted to between 4 and 5 with HCl (0.1 N). After separation into two layers, the aqueous phase was extracted with $CH_2Cl_2$ (2×25 mL). Combined organic layer was washed with de-ionized water (1×15 mL) and dried over $Na_2SO_4$. Evaporation of solvent gave a yellow solid (172.3 mg), which was subjected to preparative TLC (silica gel, Analtech, $CH_2Cl_2/MeOH=19/1$) to give a mixture of products (9) and (10) (65.5 mg, 55.8% yield). The (9) and (10) mixture (52.1 mg) was further subjected to preparative TLC (silica gel, Analtech, EtOAc/Hexane/MeOH=14/5/1) to give two fractions (9) (17.4 mg, 34% isolated yield) and (10) (18.4 mg, 35% isolated yield). (9): mass spectrum ($ES^+$; MNa, m/e: 1171.6); (10): mass spectrum (ES, $MNa^+$, m/e: 1171.6).

Figure 5:
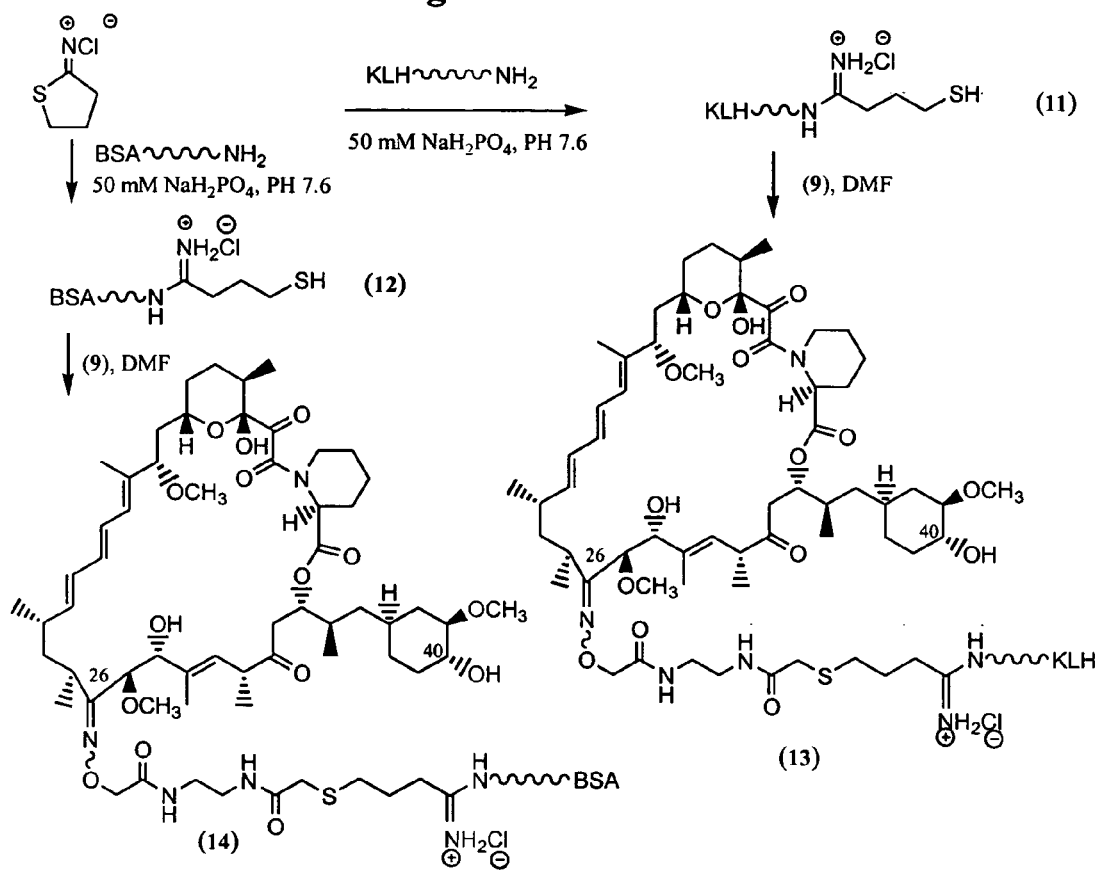
FIG. 5 is a scheme depicting another synthesis of protein derivatives of sirolimus compounds at position 26 where the proteins are KLH and BSA, respectively.

Preparation of KLH Immunogen (13) (See FIG. 5)

(a) Preparation of Thiolated KLH (11)

To KLH (40 mg) in sodium phosphate buffer solution (50 mM $NaH_2PO_4$, pH 7.6) (8 mL) was added 2-iminothiolane hydrochloride (2-IT) (12.2 mg, 0.0886 mmol) in an ice bath. The solution was stirred at room temperature under nitrogen for one hour. The thiolated KLH (KLH-SH) was purified through an equilibrated SEPHADEX G-25 column (C26×40) and was eluted with sodium phosphate buffer (50 mM NaH$_2$PO$_4$, 150 mM NaCl, 1 mM EDTA, pH 7.2). The eluted fractions from the column were monitored using a UV detector at 280 nm. Fractions containing KLH (11) were pooled to a total of 17 mL and the concentration of the protein was determined to be 3.29 mg/mL by UV detector at 280 nm.

(b) Preparation of KLH Immunogen (13)

To the KLH-SH solution (11) (4.74 mL) was added (9) (12.5 mg, 10.9 mmol) in DMF (0.5 mL) drop wise in an ice bath. After stirring at room temperature for one hour, the solution was kept stirring in a cold room (40° C.) overnight. The reaction mixture was purified through a SEPHADEX G-25 column (C26×40), which was equilibrated with a sodium phosphate buffer (100 mM NaH$_2$PO$_4$, pH 7.0). The eluted fractions from the column were monitored using a UV detector at 280 nm. A clean separation between KLH immunogen and the hapten was obtained. Fractions contained KLH immunogen (13) were pooled to a total of 12.5 mL. The concentration of the immunogen was determined by BCA Protein Concentration Assay and the hapten number by TNBS assay. The immunogen had a concentration of 0.74 mg/mL with a hapten number of 1564 and was used for the immunization of rabbits to raise antibody.

Preparation of BSA Immunogen (14) (See FIG. 5)

(a) Preparation of Thiolated BSA (12)

To BSA (40 mg) in sodium phosphate buffer solution (50 mM NaH$_2$PO4, pH 7.6) (8 mL) was added 2-Iminothiolane hydrochloride (2-IT) (23.0 mg, 0.167 mmol) in an ice bath. The solution was stirred at room temperature under nitrogen for one hour. The thiolated BSA (BSA-SH) was purified through an equilibrated SEPHADEX G-25 column (C26× 40), eluted with sodium phosphate buffer (50 mM NaH$_2$PO$_4$, 150 mM NaCl, 1 mM ethylene diamine tetraacetate (EDTA), pH 7.2) to remove excess 2-IT. The eluted fractions from the column were monitored using a UV detector at 280 nm. Fractions containing BSA (12) were pooled to a total of 20.05 mL and the concentration of the protein was determined to be 1.215 mg/mL by UV detector at 280 nm.

(b) Preparation of BSA Immunogen (14)

To the BSA-SH solution (12) (9.74 mL) was added (9) (19.3 mg, 0.0168 mmol) in DMF (0.6 mL) drop wise in an ice bath. After stirring at room temperature for one hour, the solution was kept stirring in a cold room (4° C.) for 16 hours. The reaction mixture was purified through a SEPHADEX G-25 column (C26×40), which was equilibrated with a sodium phosphate buffer (100 mM NaH$_2$PO$_4$, pH 7.0). The eluted fractions from the column were monitored using a UV detector at 280nm. A clean separation between BSA immunogen and the hapten was obtained. Fractions contained BSA immunogen (14) were pooled to a total of 30.05 mL; the concentration of the immunogen was determined by BCA Protein Concentration Assay and the hapten number by TNBS assay. The immunogen had a concentration of 0.556 mg/mL with a hapten number of 23 and was used for the immunization of rabbits to raise antibody.

Figure 6:
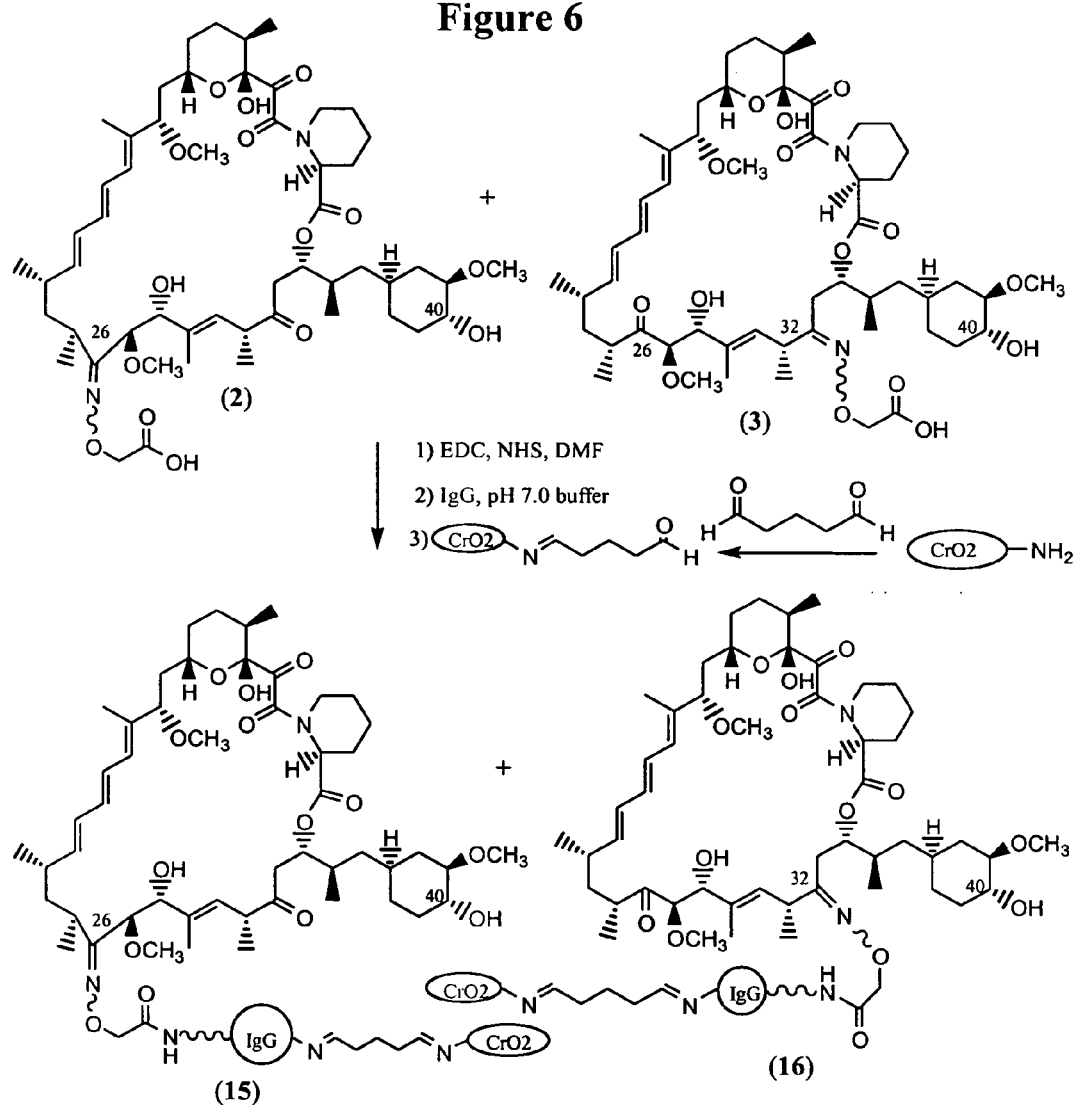
FIG. 6 is a scheme depicting the synthesis of chromium particle derivatives of sirolimus compounds at positions 26 and 32, respectively.

Preparation of Rapamycin-IgG-Chrome Slurry (15) and (16) (See FIG. 6)

To a rapamycin oxime region-isomer mixture (compound 2 and 3 prepared as described above) (12.6 mg, 0.0128 mmol) in DMF (0.5 mL) were added 1-ethyl-3-(3'-dimethylaminopropyl)carbodiimide hydrochloride (EDC) (8.58 mg, 0.045 mmol) and NHS (4.40 mg, 0.038 mmol). After stirring at room temperature for 6 hours, the solution was added into IgG (76.6 mg, 0.0005 mmol) in sodium phosphate buffer solution (10 mM NaH$_2$PO$_4$, 300 mM NaCl, pH 7.0) (7.67 mL). The mixture was rocked at room temperature overnight and then was concentrated to 3.0 mL and purified over a SEPHADEX G-25 column equilibrated in sodium phosphate buffer (10 mM NaH$_2$PO$_4$, pH 7.0). The eluted fractions from the column were monitored using a UV detector at 280 nm. A clean separation between IgG conjugate and hapten was obtained. Fractions containing the conjugate were pooled to a total of 14.8 mL, the concentration (4.06 mg/mL) of the protein, which was determined by BCA Protein Concentration Assay, was adjusted to 2 mg/mL for further conjugation.

Chrome particle raw material (CPRM) (prepared as described in U.S. Pat. Nos. 4,661,408, 4,769,165 and 5,164,299) (10 mL, 5% solid) was washed with sodium phosphate buffer (×3) by centrifugation, suspension and re-suspended to 10 mL. Glutaraldehyde (25%, 4 mL) was diluted to 10 mL with sodium phosphate buffer (10 mM NaH$_2$PO$_4$, pH 7) and was then added to the washed chrome. The mixture was rocked at room temperature for 4 hours and then was washed with sodium phosphate buffer (10 mM NaH$_2$PO$_4$, pH 7) (×3) by centrifugation, suspension and re-suspended to 10 mL. The IgG conjugate solution (10mL) was added to washed chrome and rocked at room temperature overnight.

After adding bovine gamma globulin (BGG) (30% wt/vol, 8 mL) in sodium phosphate buffer solution (10 mM NaH$_2$PO$_4$, pH 7, 8 mL), IgG-chrome conjugate was rocked at 45° C. for 4 hours. Glycine buffer (2 M, 14 mL) was then added and the slurry was rocked at room temperature for 2 hours. IgG chrome conjugate was finally washed with sodium phosphate buffer (3×20 ml) by centrifugation, suspension and finished to original volume (10 mL, 5% solid).

Figure 7:
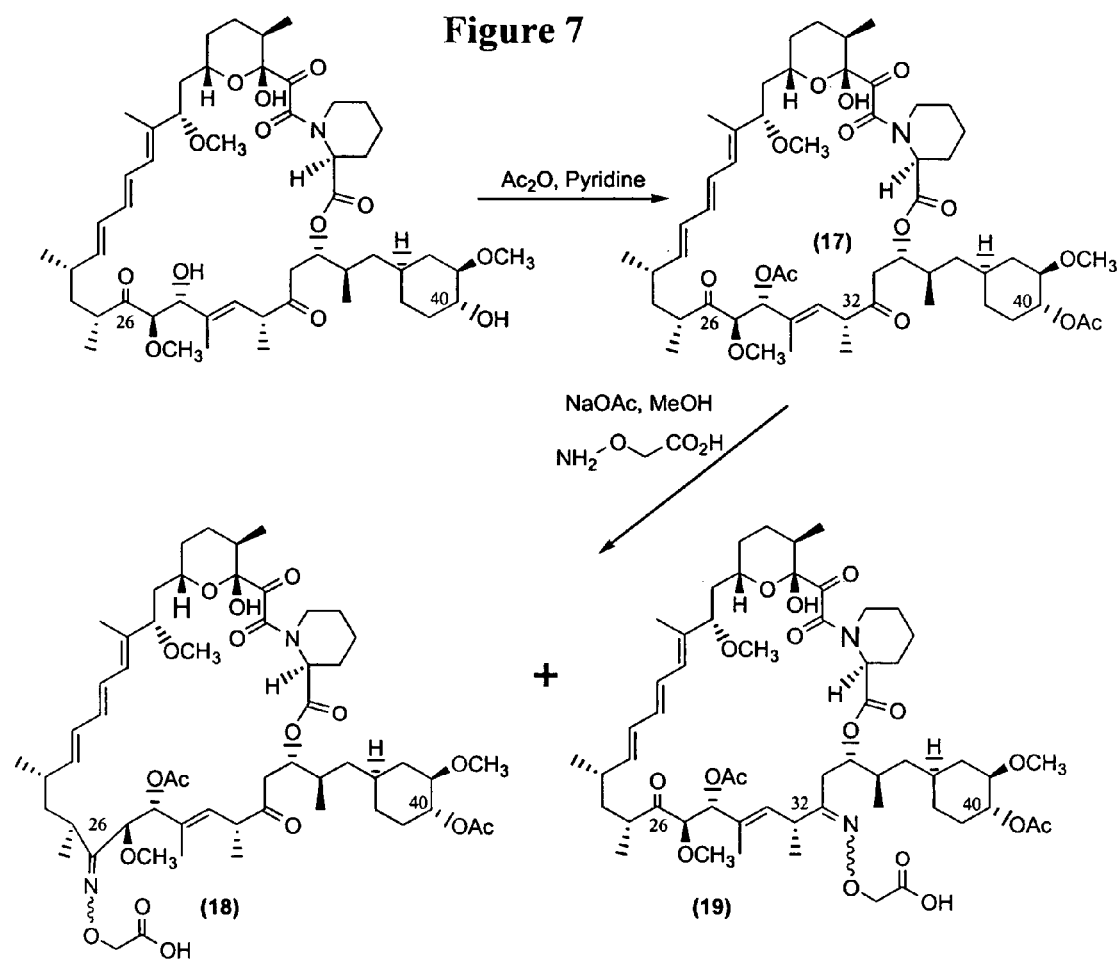
FIG. 7 is a scheme depicting another synthesis of oxime derivatives of sirolimus compounds at positions 26 and 32, respectively.

Preparation of Rapamycin Derivative (17) (See FIG. 7)

To a solution of rapamycin (17) (300 mg, 0.328 mmol) in pyridine (5 ml) was added acetic anhydride slowly (2.5 ml, 26.4 mmol) at 0–5° C. The reaction mixture was stirred at 0–5° C. for 2 hours. The excess of anhydride was decomposed by adding methanol (1 ml). The reaction mixture was poured into ice-cooled 2 N HCl (10 ml). The aqueous layer was extracted with ethyl acetate (3×60 mL). The combined organic layer was washed with de-ionized water (2×30 ml), dried over Na$_2$SO$_4$, filtered and concentrated. These products were put in high vacuum for 24 hours to give a mixture of regio-isomers (17). HPLC-MS analysis of the mixture displayed two separated peaks with the same molecule mass (MNa$^+$, 1020.8)

Preparation of Rapamycin Derivatives (18) and (19) (See FIG. 7)

To a solution of 28,40-diacetyl-rapamycin (17) (112 mg, 0.1222 mmol) and carboxymethyoxyamine hemihydrochloride (136 mg, 0.622 mmol) in MeOH (5 mL) was added sodium acetate (40 mg, 0.4878 mmol). The reaction mixture was stirred at room temperature under nitrogen atmosphere for 5 hours and the progress of the reaction was monitored by TLC (silica gel) (MeOH/CH$_2$Cl$_2$=1/9). De-ionized water (10 ml) was added into the mixture. Most of the methanol was evaporated by rotary evaporation. The aqueous layer was extracted with methylene chloride (3×30 mL). The combined organic layer was washed with de-ionized water (2×30 ml), dried over Na$_2$SO$_4$, filtered and concentrated. These products were put in high vacuum for 24 hours to give a mixture of regio-isomers (18) and (19) (120 mg). HPLC-MS analysis of the mixture displayed two separated peaks with the same molecule mass (MNa$^+$, 1093.59) indicating the occurrence of 18 and 19.

Figure 8:
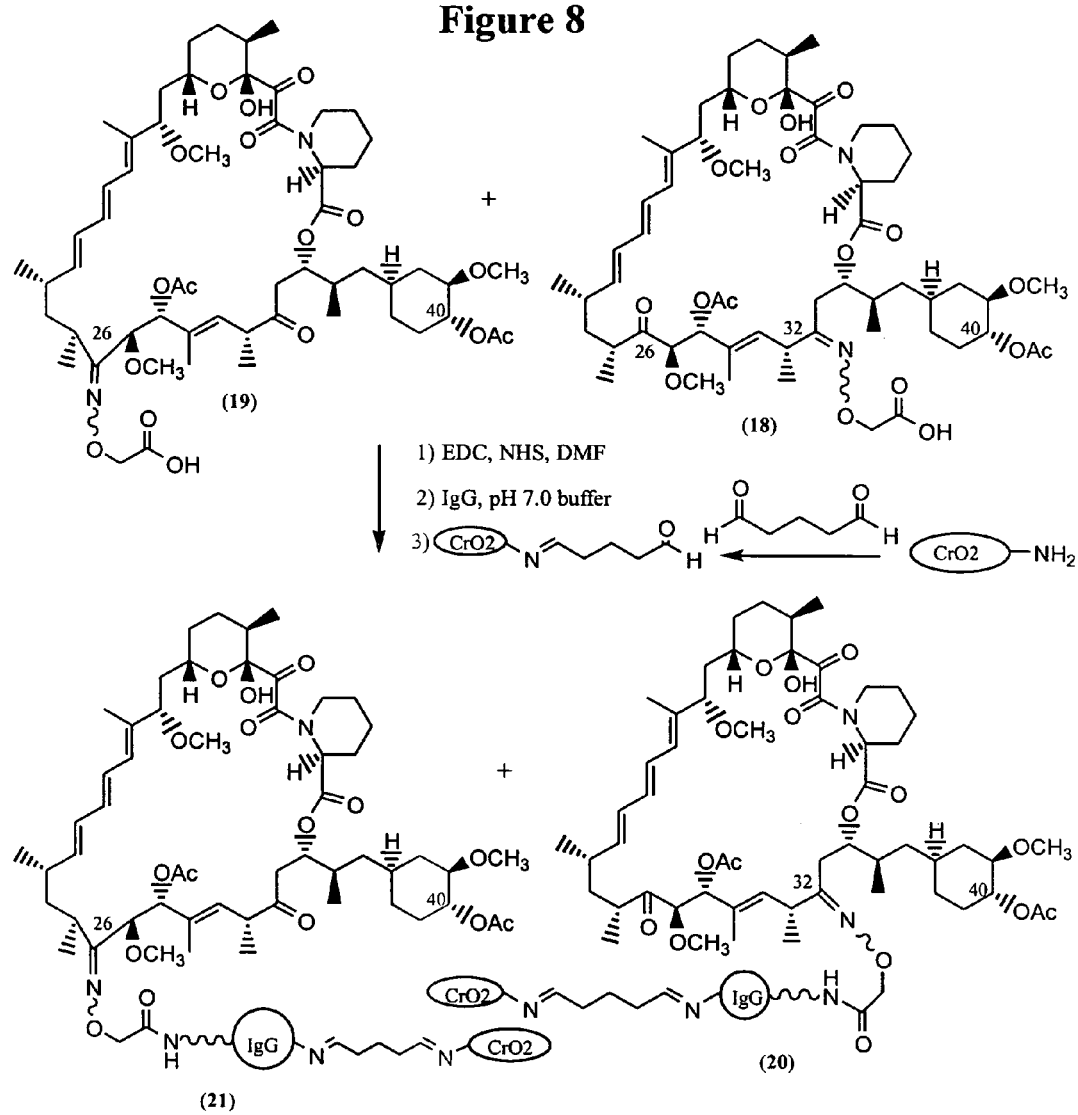
FIG. 8 is a scheme depicting the synthesis of chromium particle derivatives of sirolimus compounds at positions 26 and 32, respectively.

Preparation of Diacetyl-Rapamycin-IgG-Chrome Slurry (20) and (21) (See FIG. 8)

To a diacetyl-rapamycin oxime mixture (18) and (19) (19.9 mg, 0.0186 mmol) in DMF (0.5 mL) were added EDC (12.48 mg, 0.065 mmol) and NHS (6.41 mg, 0.056 mmol). After stirring at room temperature for 6 hours, the solution was added into IgG (111.45 mg, 0.0007 mmol) in sodium phosphate buffer solution (10 mM $NaH_2PO_4$, 300 mM NaCl, pH 7.0) (11 mL). The mixture was rocked at room temperature overnight, then concentrated to 3.0 mL and purified over a SEPHADEX G-25 column equilibrated in sodium phosphate buffer (10 mM $NaH_2PO_4$, pH 7.0). The eluted fractions from the column were monitored using a UV detector at 280 nm. A clean separation between IgG conjugate and hapten was obtained. Fractions containing the conjugate were pooled to a total of 32 mL; the concentration (3.07 mg/mL) of the protein, which was determined by BCA Protein Concentration Assay and was adjusted to 2 mg/mL for further conjugation.

Chrome particle raw material (CPRM) (10 mL, 5% solid) was washed with sodium phosphate buffer (×3) by centrifugation, suspension and re-suspended to 10 mL. Glutaraldehyde (25%, 4 mL) was diluted to 10 mL with sodium phosphate buffer (10 mM $NaH_2PO_4$, pH 7) and was then added to the washed chrome. The mixture was rocked at room temperature for 4 hours, then washed with sodium phosphate buffer (10 mM $NaH_2PO_4$, pH 7) (×3) by centrifugation, suspension and re-suspended to 10 mL. The IgG conjugate solution (10 mL) was added to washed chrome and rocked at room temperature overnight.

After adding BGG (30% wt/vol, 8 mL) in sodium phosphate buffer solution (10 mM $NaH_2PO_4$, pH 7, 8 mL), IgG-chrome conjugate was rocked at 45° C. for 4 hours. Glycine buffer (2 M, 14 mL) was then added and the slurry was rocked at room temperature for 2 hours. IgG chrome conjugate was finally washed with sodium phosphate buffer (3×10 ml) by centrifugation, suspension and finished to original volume to give slurry (20) and (21) (10 mL, 5% solid).

Figure 9:
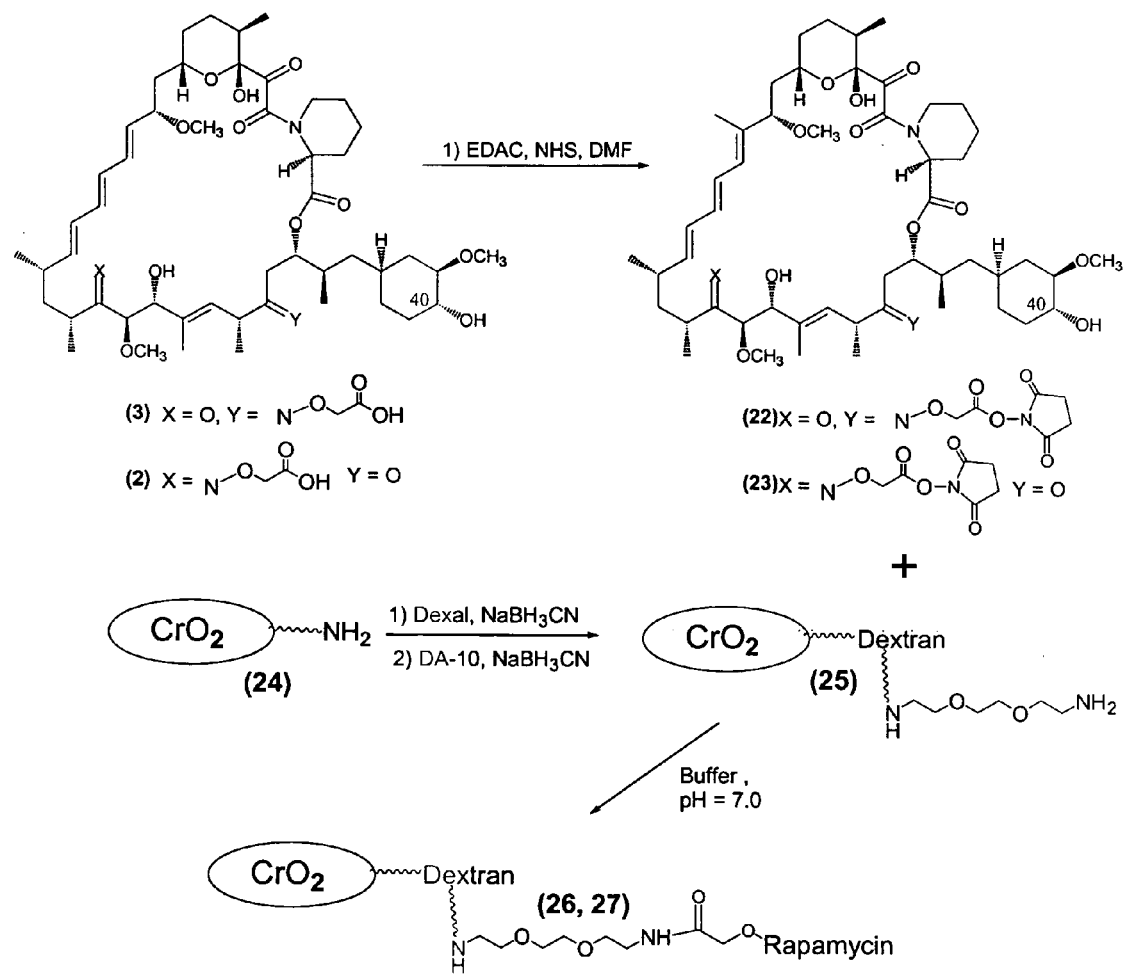
FIG. 9 is a scheme depicting the synthesis of chromium particle derivatives of sirolimus compounds at positions 26 and 32, respectively.

Preparation of Rapamycin-Dexal-Chrome Slurry (26) and (27) (See FIG. 9)

To a suspension of dexal-chrome particles (prepared by a procedure similar to that described in U.S. Pat. No. 6,231,982) (20 ml) was added $NaCNBH_3$ (113.6 mg, 1.8 mmol) and a solution of 1,2-bis(2-aminoethoxy ethane) (DA-10) (0.5 g, 3.37 mmol) in sodium phosphate buffer (20 ml, 100 mM, pH 6). The mixture was rocked at room temperature for 16 hours. The dexal-DA-10-chrome was washed with sodium bicarbonate (4×50 ml), DI water (4×50 ml) until the water pH value is 7.00. The dexal-DA-10-chrome was then washed with sodium phosphate buffer (100 mM, pH 7) (2×50 ml) and re-suspend to 20 ml for next reaction.

To a mixture of rapamycin-oxime (2) and (3) (40 mg, 0.0405 mmol) in DMF (1 mL) were added EDC (25 mg, 0.13 mmol) and NHS (12 mg, 0.104 mmol). After stirring at room temperature for 6 hours, the solution was added to the dexal-DA-10-chrome suspension in sodium phosphate buffer solution (8 ml, 100 mM, pH 7). The mixture was rocked at room temperature for 16 hours. The dexal-DA-10-rapamycin-chrome slurry (26) and (27) was washed with DI water (4×50 ml), ethanol (12×30 ml) and sodium phosphate buffer (100 mM, pH 7) (4×50 ml) and re-suspend to 7.5 ml (5%). solid).

Preparation of Rapamycin-O-(6-Atom-Linker)-Oxime 31 and 32.

Rapamycin (79.6 mg. 87, μmol) dissolved in 1 ml MeOH, and N-(-2-aminooxy-ethyl)-2-bromo-acetamide (300 μmol) dissolved in 1.5 ml MeOH was added via syringe followed by anhydrous NaOAc (23.4 mg, 285 μmol). The mixture was stirred for 16 hours at 22° C. and concentrated to dryness under reduced pressure. The residue was subjected to preparative TLC ($SiO_2$, EtOAc-Hexane, 5:2) to give two fractions 1 (44 mg, 46%) and 2 (20 mg, 21%) as white solids together with 18 mg (23%) of re-isolated Rapamycin. Mass spectrum, (1, FAB-NBA), m/e 1000.9 ($MNa^+$, 60). Mass spectrum (2, FAB-NBA), m/e 1000.9 ($MNa^+$, 80). The depictions in the examples below show a portion of the entire rapamycin molecule. For example, immediately below is rapamycin with the linker at position 32 (compound 31) and position 26 (compound 32).

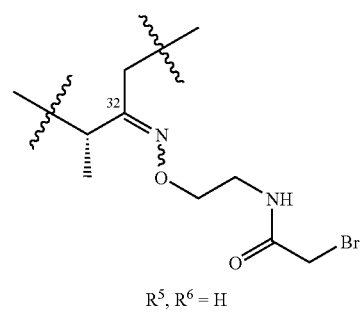

31

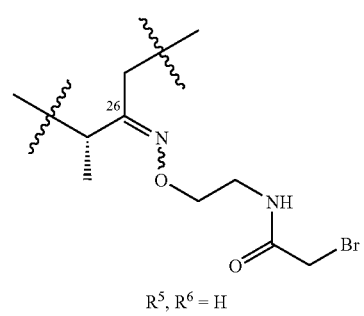

32

Preparation of Biotin-CMO-Rapamycin 35.

Biotin (10 mg, 25.1 μmol) was dissolved in 0.3 ml DMF. Compound 3 (24.7 mg, 25.1 μmol) followed by N-Hydroxysuccinimide (3.0 mg, 25.1 μmol) and 1-Ethyl-3-(3-dimethylaminopropyl)-carbodiimide (9.6 mg, 50.2 μmol) were added to the biotin-DMF solution at 0° C. The mixture was stirred for 1 hour at 0° C., then at 3 hours at 22° C. The mixture was applied to a preparative TLC plate ($SiO_2$, 1000 μm, EtOAc-MeOH, 8:1). The major fraction 35 is isolated as a white powder and was shown to be the desired product.

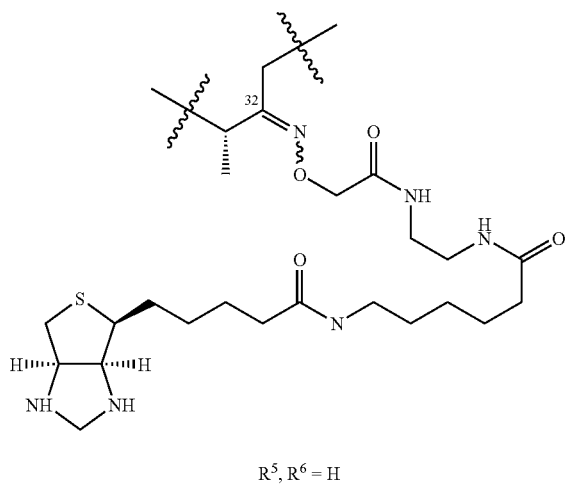

R⁵, R⁶ = H

Figure 10:
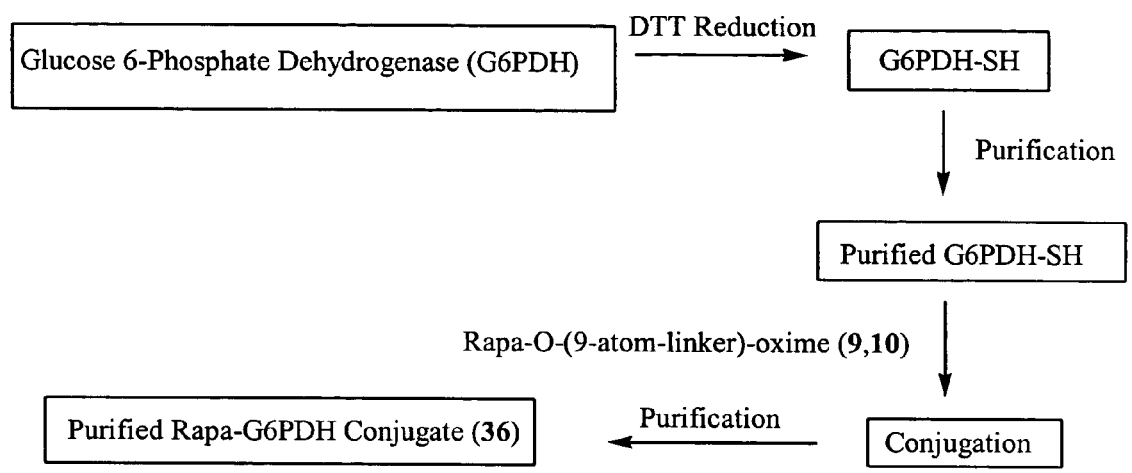
FIG. 10 is a scheme depicting the synthesis of a G6PDH conjugate of sirolimus.

Preparation of G6PDH -Rapamycin-O-(9-Atom-Linker)-Oxime Conjugate (36) (FIG. 10)

G6PDH (2.2 mL, 10 mg/mL, Genemed Biotechnologies, Inc., (South San Francisco Calif.) was buffer exchanged in an Amica (YM 8050) with PBS buffer (50 mM $NaH_2PO_4$, 1 mM EDTA, pH 7.25) (3×50 mL), then the concentration of the enzyme was measured by absorbance at 280 nm and adjusted to 5.0 mg/mL (6.91 mL) with the same buffer solution. Dithiothreitol (DTT) (500 mM, 69.1 μL) was added into the enzyme solution and the mixture was set in refrigerator overnight. Excess DTT was removed by an Amica (YM 8050) through buffer (50 mM $NaH_2PO_4$, 1 mM EDTA, 25 μM DTT, pH 7.25) exchange. The concentration of the purified protein was measured by absorbance at 280 nm (6.8 mg/mL. 3.5 mL) and adjusted to 3 mg/mL (7.9mL) with PBS buffer (50 mM $NaH_2PO_4$, 1 mM EDTA, 25 μM DTT, pH 7.25). Rapamycin-O-(9-atom-linker)-oxime (9/10) (6.21 mg) in DMF (0.2 mL) was added into the above purified enzyme (2.63 mL, 3 mg/mL) and the solution was rocked in cold room (4° C.) for 16 hours. The progress of the reaction was monitored by the disappearance of free thiol (—SH) using 2, 2'-dithiodipyridine (DTDP). The G6PDH conjugate was purified by a pre-equilibrated column (Sephadex G-25) eluted with sodium phosphate buffer (50 mM $NaH_2PO_4$, pH 7.0). The purification ran in a cold room and the fractions contained enzyme conjugate were pooled (8.1 mg) and concentration of the conjugate was found to be 1.33 mg/mL by absorbance at 280 nm. The enzyme activity of the conjugate was measured by the change in absorbance at 340 nm against native enzyme G6PDH and found to be 93.6%.

EMIT Assay Using Rabbit Polyclonal Antibodies Raised Against a C-26-Rapamycin-Oxime Immunogen Prepared in a Manner Similar to that Described Above:

An enzyme conjugate was generated by crosslinking a mixture of C-26 and C-32 rapamycin-oxime haptens to glucose-6-phosphate dehydrogenase in a procedure similar to that described above. The conjugate was diluted in a standard EMIT dilution buffer to yield a maximum enzyme activity rate of 0.486 absorbance units per minute or 486 mAU per minute as measured on the Cobas MIRA S analyzer (Roche Diagnostics Systems, Inc., Branchburg, N.J.). The serum from rabbit #1514 (injected with immunogen according to known procedures for polyclonal antibody production) was diluted 1:10 in the standard EMIT antibody diluent which contains the necessary co-factors for G6PDH activity. When this antibody was incubated with the conjugate in the absence of any rapamycin in the sample, the enzyme activity rate was reduced to 329 mAU/min, which is an inhibition of 32.30%. When 200 ng/mL of rapamycin was spiked in the sample, the enzyme activity rate was increased to 354 mAU/min, which is an inhibition of 26.40%. This change in inhibition from 32.30% to 26.40% is a significant difference and demonstrates the effectiveness of the above polyclonal antibody and enzyme conjugate for EMIT assay techniques.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

The invention claimed is:

1. A compound comprising a moiety, selected from the group consisting of poly(amino acid) label moieties, non-poly(amino acid) label moieties, poly(amino acid) immunogenic carriers, non-poly(amino acid) immunogenic carriers, non-label poly(amino acid) moieties, and non-immunogenic carrier poly(amino acid) moieties linked to a sirolimus compound at position 26 by means of a bond or a linking group.

2. A compound according to claim 1 wherein the moiety is linked to the sirolimus compound at position 26 by a linking group that comprises an oxime functionality.

3. A compound according to claim 1 wherein the moiety is a non-poly(amino acid) immunogenic carrier selected from the group consisting of polysaccharides, nucleic acids and particles or a poly(amino acid) immunogenic carrier selected from the group consisting of albumins and globulins.

4. An antibody raised against a compound according to claim 1 wherein the moiety is a poly(amino acid) immunogenic carrier or a non-poly(amino acid) immunogenic carrier linked at position 26.

5. A compound of structure I:

[Structure I: sirolimus-derived macrocycle with positions labeled 26, 32, 40, groups OCH₃, OR⁶, OR⁵, A¹, A², OH, H, N, O]

wherein A¹ is oxo and A² is a group of the formula:

[Structure Ia: $=N-O-[C(R_2R_3)]_n-C(O)-[NR_4(CR_2R_3)_q]_m-[NR_4]_p-C(O)-[NR_4]_t-[C(R_2R_3)]_u-D_y-[C(R_2R_3)]_v-[C(G)]_x-O_z-[C(R_2R_3)]_w-R_1$]

and wherein:
n, q, u, v and w are independently 0 to about 12,
m is 0 or 1,
p is 0 or 1,
t is 0 or 1,
y is 0 to about 5,
x is 0 or 1,
z is 0 or 1,
D is O or S,
G is O or NR²,
R¹ is a moiety, selected from the group consisting of functional groups, poly(amino acid) label moieties, poly(amino acid) immunogenic carriers, non-poly (amino acid) label moieties, and non-poly(amino acid) immunogenic carriers, or

[Structure II: biotin-derived moiety with amide linkage to alkyl chain]

R² and R³ are independently selected from hydrogen, $C_{1-10}$ alkyl, benzyl, OH, halogen, $C_{1-6}$ alkoxy; $C_{3-10}$ alkenyl, and $C_{3-10}$ alkynyl, R⁴ is independently hydrogen, $C_{1-10}$ alkyl, benzyl, $C_{3-10}$ alkenyl, $C_{3-10}$ alkynyl; and R⁵ and R⁶ are independently selected from hydrogen; phenyl; substituted phenyl in which the substituents are X, Y and Z; 1- or 2-naphthyl; substituted 1- or 2-naphthyl in which the substituents are X, Y and Z; $C(O)C_{1-6}$ alkyl; $C_{1-10}$ alkyl; $C_3$–$C_{10}$ cycloalkyl; substituted $C_{1-10}$ alkyl in which one or more substituent(s) is(are) selected from hydroxy, oxo, $C_{1-6}$-alkoxy; phenyl, substituted phenyl in which the substituents on phenyl are X, Y and Z and $OC(O)C_{1-6}$ alkyl; $C_{3-10}$ alkenyl; $C_{4-10}$ cycloalkenyl; substituted $C_{3-10}$ alkenyl in which one or more substituent(s) is(are) selected from hydroxy, oxo, $C_{1-6}$-alkoxy, phenyl, substituted phenyl in which the substituents on phenyl are X, Y and Z and $OC(O)C_{1-6}$ alkyl; $C_{3-10}$ alkynyl; and substituted $C_{3-10}$ alkynyl in which one or more substituent(s) is(are) selected from hydroxy, oxo, $C_{1-6}$-alkoxy, phenyl, substituted phenyl, in which the substituents on phenyl are X, Y and Z and $OC(O)C_{1-6}$ alkyl;

X, Y and Z are independently selected from: hydrogen; $C_{1-7}$ alkyl; $C_{2-6}$ alkenyl; halogen; CN; C(O)H; perhalosubstituted groups; $SR^7$, wherein $R^7$ is hydrogen, $C_{1-6}$ alkyl, $CF_3$ or phenyl; $SOR^7$, wherein $R^7$ is as defined above; $SO_2R^7$, wherein $R^7$ is as defined above; $CONR^5R^6$, wherein $R^5$ and $R^6$ are as defined above; —$(CH_2)_r OR^8$, wherein $R^8$ is hydrogen, $C_{1-3}$ alkyl; hydroxy-$C_{2-3}$ alkyl, and r is 0–2; $C_{1-3}$ alkyl; hydroxy-$C_2$-3 alkyl; $CH(OR^9)(OR^{10})$, wherein $R^9$ and $R^{10}$ are $C_{1-3}$ alkyl or taken together form an ethyl or propyl bridge; —$(CH_2)_r OC(O)R^8$, wherein $R^8$ and r are as defined above, and —$(CH_2)_r C(O)OR^8$, wherein $R^8$ and r are as defined above.

6. A compound according to claim 5 wherein the moiety is an immunogenic carrier selected from the group consisting of poly(amino acids), polysaccharides, nucleic acids and particles.

7. A compound according to claim 5 wherein the moiety is a poly(amino acid) immunogenic carrier selected from the group consisting of bovine serum albumin, keyhole limpet hemocyanin, egg ovalbumin, and bovine gamma-globulin.

8. An antibody raised against a compound according to claim 5 wherein the moiety is a poly(amino acid) immunogenic carrier or a non-poly(amino acid) immunogenic carrier at position 26.

9. sirolimus compound according to claim 5 wherein the sirolimus compound of structure I is linked to a polysaccharide by means of Ia and wherein the polysaccharide is further linked to a particle.

10. A sirolimus compound according to claim 9 wherein the particle is a chrome particle.

11. A compound according to claim 5 wherein the moiety is a poly(amino acid) label moiety that is an enzyme.

12. A compound according to claim 5 wherein group Ia has the formula:

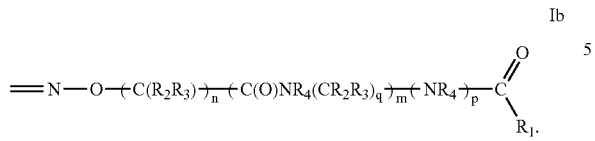
Ib

13. A compound according to claim 5 wherein group Ia has the formula:

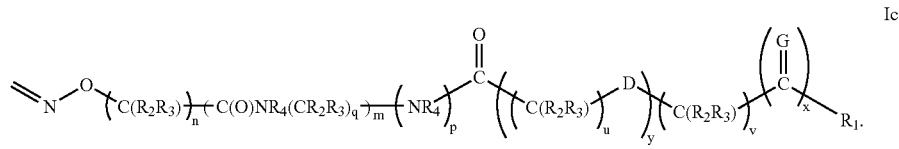
Ic

14. A compound according to claim 13 wherein group Ia has the formula:

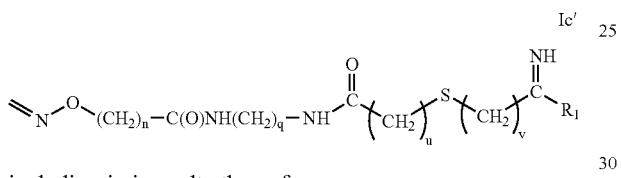
Ic′ including imine salts thereof.

15. A compound according to claim 5 wherein group Ia has the formula:

Id

16. A compound according to claim 5 wherein group Ia has the formula:

Id′ wherein n is 1, u is 2, y is 2 and v is 1 and wherein $R^1$ is linked through an amine moiety of $R^1$.

17. A kit comprising an antibody for a sirolimus compound and a compound according to claim 5 wherein the moiety is a poly(amino acid) label or a non-poly(amino acid) label.

* * * * *